US012700499B2

(12) United States Patent
Kwan et al.

(10) Patent No.: US 12,700,499 B2
(45) Date of Patent: Aug. 4, 2026

(54) MAINTENANCE SYSTEMS AND METHODS FOR MEDICAL DEVICES

(71) Applicant: Fisher & Paykel Healthcare Limited, Auckland (NZ)

(72) Inventors: Ian Lee Wai Kwan, Auckland (NZ); Warushahennedige Hansinie Soysa, Auckland (NZ); Wenjie Robin Liang, Auckland (NZ); Dexter Chi Lun Cheung, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 0 days.

(21) Appl. No.: 18/530,887

(22) Filed: Dec. 6, 2023

(65) Prior Publication Data

US 2024/0161919 A1      May 16, 2024

Related U.S. Application Data

(63) Continuation of application No. 15/761,796, filed as application No. PCT/NZ2016/050154 on Sep. 21, 2016, now abandoned.

(Continued)

(51) Int. Cl.
G16H 40/40          (2018.01)
G06F 11/22          (2006.01)
(Continued)

(52) U.S. Cl.
CPC ............. G16H 40/40 (2018.01); G06F 11/22 (2013.01); G06F 17/40 (2013.01); G06Q 10/20 (2013.01); G06Q 30/0633 (2013.01)

(58) Field of Classification Search
CPC ........ G16H 10/00; G16H 10/20; G16H 10/40; G16H 15/00; G16H 20/00; G16H 20/10;
(Continued)

(56) References Cited

U.S. PATENT DOCUMENTS 5,645,571 A      7/1997   Olson et al.
8,788,236 B2     7/2014   Vij et al.
(Continued)

FOREIGN PATENT DOCUMENTS

EP          0893772 A2      1/1999
WO      WO 2017/052385      3/2017

OTHER PUBLICATIONS

IEEE 2007, "IEEE Recommended Practice for Electric Systems in Health Care Facilities," in IEEE Std 602-2007 (Revision of IEEE Std 602-1996) , vol. No., pp. 1-436, Aug. 29, 2007, doi: 10.1109/ IEEESTD.2007.4299432.*

(Continued)

*Primary Examiner* — Robert W Morgan
*Assistant Examiner* — Charles P Coleman
(74) *Attorney, Agent, or Firm* — Knobbe, Martens, Olson & Bear, LLP

(57)          ABSTRACT

A maintenance system for a medical device includes a user device configured to communicate with the medical device and execute maintenance tasks on the medical device and communicate with a user via a user interface of the user device or the medical device. The maintenance tasks may be executed by either device or both devices, and communication with a user may occur via a user interface of either device or both devices. The system may also include a server configured to communicate with one or both of the user device and the medical device. The maintenance tasks may include an electrical safety check, a physical check, a performance check, and a functional check. Examples of functional checks include validation of a transient current detector and a thermal cutout.

20 Claims, 14 Drawing Sheets

Related U.S. Application Data

(60) Provisional application No. 62/321,596, filed on Apr. 12, 2016, provisional application No. 62/290,819, filed on Feb. 3, 2016, provisional application No. 62/221,519, filed on Sep. 21, 2015.

(51) Int. Cl.
G06F 17/40 (2006.01)
G06Q 10/20 (2023.01)
G06Q 30/0601 (2023.01)

(58) Field of Classification Search
CPC ........ G16H 20/13; G16H 20/17; G16H 30/00; G16H 40/00; G16H 50/00; G16H 70/00; G16H 40/40; G16H 80/00; G06Q 50/22–24; G06Q 10/20; G06Q 30/0633; G06F 11/22; G06F 17/40
USPC .................................................. 705/2, 3, 20
See application file for complete search history.

(56) References Cited

U.S. PATENT DOCUMENTS

| | | | |
|---|---|---|---|
| 2004/0033799 A1 | 2/2004 | Fontius | |
| 2005/0103354 A1 | 5/2005 | Miyauchi et al. | |
| 2006/0149808 A1 | 7/2006 | Weiner et al. | |
| 2006/0206389 A1 | 9/2006 | Elssner et al. | |
| 2009/0099867 A1 | 4/2009 | Newman | |
| 2009/0157695 A1 | 6/2009 | Roberts | |
| 2009/0177769 A1* | 7/2009 | Roberts .................. | G16H 40/40 709/224 |
| 2012/0105097 A1* | 5/2012 | Hancock ................ | G01R 31/42 324/764.01 |
| 2012/0146251 A1 | 6/2012 | Heine et al. | |
| 2012/0158089 A1 | 6/2012 | Bocek et al. | |
| 2012/0197580 A1 | 8/2012 | Vij et al. | |
| 2013/0268890 A1 | 10/2013 | Jensen et al. | |
| 2014/0032232 A1 | 1/2014 | Brown et al. | |
| 2014/0166006 A1 | 6/2014 | Meier | |
| 2014/0226248 A1* | 8/2014 | Hameed .................. | H02H 1/00 361/115 |
| 2014/0266713 A1 | 9/2014 | Sehgal et al. | |
| 2014/0266777 A1 | 9/2014 | Gettings et al. | |
| 2014/0288619 A1 | 9/2014 | Johnson et al. | |
| 2015/0045634 A1 | 2/2015 | Goldberg et al. | |
| 2015/0120318 A1 | 4/2015 | Toyama | |
| 2015/0371198 A1* | 12/2015 | Jensen ................ | G06F 3/04842 705/305 |
| 2016/0173816 A1 | 6/2016 | Huenerfauth et al. | |
| 2018/0286510 A1 | 10/2018 | Kwan et al. | |
| 2022/0375593 A9 | 11/2022 | Butka et al. | |
| 2023/0254378 A1* | 8/2023 | Durrant .................. | G16H 40/40 709/217 |

OTHER PUBLICATIONS

Liu et al. 2018, "A Patent Analysis of Prognostics and Health Management (PHM) Innovations for Electrical Systems," in IEEE Access, vol. 6, pp. 18088-18107, 2018, doi: 10.1109/ACCESS.2018. 2818114.*

International Search Report and Written Opinion in corresponding International Patent Application No. PCT/NZ2016/050154, mailed Jan. 6, 2017, in 13 pages.

Blount et al. 2007, "Remote health-care monitoring using Personal Care Connect," in IBM Systems Journal, vol. 46, No. 1, pp. 95-113, 2007, doi: 10.1147/sj.461.0095.

Chen 2008, "A novel network module for medical devices," 2008 30th Annual International Conference of the IEEE Engineering in Medicine and Biology Society, Vancouver, BC, Canada, 2008, pp. 1553-1556, doi: 10.1109/IEMBS.2008.4649466.

Al-Taee et al. 2011, "Mobile phone-based health data acquisition system using Bluetooth technology," 2011 IEEE Jordan Conference on Applied Electrical Engineering and Computing Technologies (AEECT), Amman, Jordan, 2011, pp. 1-6, doi: 10.1109/ AEECT. 2011.6132524.

* cited by examiner

500

Begin functional
check process — 505

Set up
functional check — 510

Execute speaker test — 515

Execute therapy touch
test — 520

Did
therapy touch test
pass? — 530

Yes

No

Execute mute touch
test — 535

Execute color test — 540

Execute LED test — 545

End functional check
progress — 550

805

Client

810

Server

830

810

812

Dashboard

814

Functional Check

816

Physical and Safety Check

818

Performance Check

Device Data Service

820

MAINTENANCE SYSTEMS AND METHODS FOR MEDICAL DEVICES

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

FIELD OF THE DISCLOSURE

The present disclosure generally relates to maintenance systems and methods for medical devices. More particularly, the present disclosure relates to maintenance systems and methods that enable a technician or other user to undertake maintenance tasks associated with a respiratory assistance device.

BACKGROUND

To ensure reliability of a medical device, maintenance of the device may be undertaken. Over the life of a medical device a technician or other user may need to perform maintenance numerous times. Maintenance ensures continued safe operation of the device, as well as opportunities to diagnose any unexpected problems with the device which can then be remedied. Failure to undertake maintenance when recommended or required can lead to the medical device functioning in an unsafe or suboptimal manner.

There are systems known in the art that are purpose-built for performing limited maintenance tasks on medical devices. Such systems can be expensive, difficult to update, and easy to misplace.

SUMMARY

Maintenance systems and methods are disclosed that perform maintenance tasks for medical devices. A maintenance system may connect or communicate with a medical device, such as a respiratory humidifier. A maintenance system may execute, or enable or assist in the execution of a maintenance task related to a medical device, such as a diagnostic test. A maintenance task may involve user input or it may be autonomous.

A maintenance system for a medical device may comprise one or more aspects of the medical device and/or one or more aspects of a user device. A user of the maintenance system may interact with a user interface of the medical device and/or a user interface of the user device. The maintenance system may execute a maintenance task comprising a maintenance check, including at least one of an electrical safety check, a physical check, a functional check, and a performance check. A result of the maintenance check, and any associated information, may be displayed to the user via the user interface. The result may be communicated to and/or stored on a device, such as one or more of the medical device, the user device, a server, or another device such as a storage device.

A maintenance system may execute one or more maintenance tasks on a medical device without the use of a user device or a server, unless otherwise stated. The one or more maintenance tasks may be executed on a user interface located on the medical device.

A maintenance system for a medical device may execute, for example, a maintenance task comprising a maintenance check to validate correct operation of a system health protection component associated with a medical device, such as a transient current detector. A system health protection component is sometimes referred to as a fault protection component, and for the purposes of this disclosure the two terms should be considered interchangeable.

A maintenance system for a medical device may execute, for example, a maintenance task comprising a maintenance check to validate proper functioning of a component, such as a thermal cutout device for a heater associated with a medical device.

A maintenance system for a medical device may execute one or more maintenance tasks, including but not limited to multiple maintenance tasks in sequence, multiple maintenance tasks in synchrony, or any combination thereof. A maintenance task may comprise one of the maintenance checks disclosed herein or another maintenance check, or other action, suitable for maintenance of a medical device.

According to at least one aspect of the present disclosure, a maintenance system for a medical device can have one, some, or all of the following features, as well as other features described herein. The medical device comprises a processor and a user interface. The maintenance system comprises a user device, the user device comprising a processor and a user interface. The processor of the user device is configured to communicate with the processor of the medical device. At least one of the processor of the user device and the processor of the medical device is configured to execute one or more maintenance tasks on or for the medical device. At least one of the processor of the user device and the processor of the medical device is configured to receive information from or provide information to a user via at least one of the user interface of the user device and the user interface of the medical device.

The maintenance system may comprise a server, the server comprising a processor. The server may comprise a user interface. The processor of the server may be configured to communicate with at least one of the processor of the user device and the processor of the medical device. The processor of the server may be configured to execute one or more maintenance tasks on or for the medical device. The processor of the server may be configured to receive information from or provide information to a user via at least one of the user interface of the user device, the user interface of the medical device, and the user interface of the server. Each of the one or more maintenance tasks may comprise one of an electrical safety check, a physical check, a performance check, or a functional check. The functional check may comprise validating the operation of a system health protection component of the medical device. The system health protection component may be configured to respond to an unexpected condition. An unexpected condition is sometimes referred to as a fault condition, and for the purposes of this disclosure the two terms should be considered interchangeable. At least one of the user device and the medical device may be configured to generate or simulate an unexpected condition as part of the functional check. The system health protection component may comprise a transient current detector. The system health protection component may comprise a thermal cutout device. The functional check may comprise validating the operation of one or more mechanical components of the medical device. The one or more mechanical components may comprise a touch screen, a button, a color display, a speaker, and a light-emitting diode.

According to at least one aspect of the present disclosure, a method of validating the operation of a system health protection component of a medical device can have one, some, or all of the following features, as well as other features describe herein. The system health protection component is configured to respond to an unexpected condition. The method comprises generating the unexpected condition. The method comprises determining a response of the system health protection component to the unexpected condition. The method comprises reporting the response to a user via a user interface. A method is sometimes referred to as a process, and for the purposes of this disclosure the two terms should be considered interchangeable.

The system health protection component may comprise a transient current detector. Generating the unexpected condition may comprise generating a transient current or an overcurrent. Determining the response of the transient current detector may comprise determining whether the transient current detector has activated a current interrupter. The system health protection component may comprise a thermal cutout. Generating the unexpected condition may comprise supplying power to a heating element. Determining the response of the thermal cutout may comprise repeatedly determining whether the thermal cutout has tripped or whether a timer has exceeded a predetermined maximum time value. The method may comprise, after determining that the thermal cutout has tripped, instructing a user to reset the thermal cutout device.

A maintenance system may function to replace hardcopy versions of a Product Technical Manual (PTM) by providing access to PTM content through the user interface of the user device, the user interface of the medical device, or the user interface of the server. A benefit of a maintenance system that replaces hardcopy versions of a PTM includes the ability to update the content of the PTM and verify the version of the PTM over the Internet. Hospital maintenance staff currently must rely on hardcopy versions of the PTM when performing maintenance tasks for medical devices. Updates to the content of a hardcopy PTM currently require the delivery of a hardcopy version of the updated PTM to hospital maintenance staff. Alternatively, an electronic document of the updated PTM may be emailed to the hospital maintenance staff. However, either method requires reliance on the hospital staff to replace the older, non-updated version of the PTM with the version of the PTM containing the updated content. A maintenance system capable of updating the PTM over the Internet provides the opportunity to update the content of the PTM and verify the version of the PTM without having to rely on the hospital maintenance staff. Furthermore, a maintenance system provides additional benefits, such as reducing the number of manual tasks required to be performed by the hospital maintenance staff, automatically gathering data and preparing a maintenance report for review, and assuring uniformity of prepared maintenance report data over time and across hospital maintenance staff, hospital wards, and hospitals, in general.

According to one aspect, there is provided a maintenance system for a medical device. The maintenance system comprises a user device, the user device including a processor and a user interface; and a server comprising a processor; wherein the processor of the server is configured to establish a connection between a processor of the medical device and the processor of the user device; generate user interface information to cause one or more user interface elements to be displayed by the user interface of the user device, the one or more interface elements prompting a user at the user device to perform an action. Further, the processor of the server is configured to, in response to the performed action, receive status information from the processor of the medical device; using the received status information, determine a status of a component of the medical device; based upon the determined status, determine whether the component is in need of replacement; and in response to a determination that the component is in need of replacement, automatically initiate an order for a replacement component for the medical device.

The processor of the server may be configured to automatically initiate an order for a replacement component for the medical device by generating user interface information to cause one or more user interface elements to be displayed by a user interface of a second user device associated with a second user, the one or more user interface elements prompting the second user to confirm the order.

The processor of the server may further be configured to generate user interface information to cause the user to input one or more values at the user interface of the user device, the one or more values being used to perform one or more diagnostic procedures on the medical device.

The user device may be remote from the medical device.

The status of the component may comprise a remaining operational life of the component. In which case, determining whether the component is in need of replacement may comprise determining if the remaining operational life of the component is under a threshold value.

The processor of the server may further be configured to determine whether the medical device is associated with account information.

According to one aspect, there is provided a maintenance system that provides automated maintenance for a medical device. The maintenance system comprises a processor configured to execute one or more maintenance tasks for the medical device and communicate with a user via a user interface.

The processor may be housed within the medical device. Alternatively, the processor may be housed within a user device that is separate from the medical device, the user device comprising a user interface, and wherein the medical device comprises a separate processor. In this latter case, the maintenance system may comprise a server, the server comprising a server processor, the server processor configured to communicate with the processor of the medical device. The maintenance system may further comprise a server comprising a server processor, the server processor configured to communicate with one or both of the processor housed in the user device and the processor housed in the medical device.

Each of the one or more maintenance tasks may comprise one of an electrical safety check, a physical check, a performance check, or a functional check. Such an electrical safety check may comprise evaluating the electrical functionality of the medical device. Such a physical check may comprise evaluating one or more physical aspects of the medical device. The one or more physical aspects of the medical device may include a power cable, a heater wire adapter, a housing, a front panel, a sensor cartridge, or a general condition.

Such a performance check may comprise validating an operation of a system health protection component of the medical device, the system health protection component being configured to respond to an unexpected condition.

At least one of the user device and the medical device may be configured to generate or simulate an unexpected condition as part of validating the operation of the system health protection component.

The system health protection component may comprise a transient current detector and/or a thermal cutout.

5

6

The functional check may comprise validating an operation of one or more mechanical components of the medical device. The one or more mechanical components may comprise a touch screen, a button, a color display, a speaker, and a light-emitting diode.

The maintenance system may be configured to execute multiple maintenance tasks in sequence, multiple maintenance tasks in synchrony, or any combination thereof.

According to one aspect, there is provided a maintenance system for a medical device, the medical device comprising a user interface; and a processor configured to execute one or more maintenance tasks on or for the medical device and receive information from or provide information to a user via the user interface.

The maintenance system may comprise a server, the server comprising a processor, the processor of the server configured to communicate with the processor of the medical device.

Each of the one or more maintenance tasks may comprise one of an electrical safety check, a physical check, a performance check, or a functional check. The electrical safety check may comprise evaluating the electrical functionality of the medical device. The physical check may comprise evaluating one or more physical aspects of the medical device. The one or more physical aspects of the medical device may include a power cable, a heater wire adapter, a housing, a front panel, a sensor cartridge, or a general condition. The performance check may comprise validating an operation of a system health protection component of the medical device, the system health protection component being configured to respond to an unexpected condition. At least one of the user device and the medical device may be configured to generate or simulate an unexpected condition as part of validating the operation of the system health protection component. The system health protection component may comprise a transient current detector and/or a thermal cutout. The functional check may comprise validating an operation of one or more mechanical components of the medical device. The one or more mechanical components may comprise a touch screen, a button, a color display, a speaker, and a light-emitting diode.

The maintenance system may be configured to execute multiple maintenance tasks in sequence, multiple maintenance tasks in synchrony, or any combination thereof.

According to one aspect, there is provided a method of executing one or more maintenance tasks for a medical device, the medical device comprising a processor and a user interface. The method comprises establishing a connection with the processor of the medical device; generating user interface information to cause one or more user interface elements to be displayed by a user interface of a user device, the one or more interface elements prompting a user of the user device to perform an action; receiving status information from the processor of the medical device in response to the action; and recording the received status information.

The method may comprise determining if the one or more maintenance tasks has recently been performed. The one or more maintenance tasks may comprise one of an electrical safety check, a physical check, a performance check, or a functional check.

The physical check may comprise evaluating one or more physical aspects of the medical device. In this case, the method may comprise instructing the user to inspect the medical device for one or more issues with one or more physical aspects of the medical device; and prompting the user to input a result or a description of the one or more issues. The one or more physical aspects of the medical device may include a power cable, a heater wire adapter, a housing, a front panel, a sensor cartridge, or a general condition.

The method may comprise prompting a user to set up the maintenance task; determining whether the user properly set up the maintenance task; executing the maintenance task; and displaying one or more results of the maintenance task to the user via the user interface.

A said electrical safety check may comprise evaluating the electrical functionality of the medical device. In this case, the method may comprise determining whether the electrical safety check passed; presenting the user with one or more troubleshooting suggestions via the user interface in response to an electrical safety check failure; and prompting the user to indicate whether the one or more troubleshooting suggestions identified the reason for the electrical safety check failure.

A said functional check may comprise validating an operation of one or more mechanical components of the medical device. The one or more mechanical components may comprise a touch screen, a button, a color display, a speaker, and a light-emitting diode.

The method may comprise executing a speaker test; executing a therapy touch screen test; determining whether the therapy touch screen test passed; executing a mute touch screen test in response to passing the therapy touch test; executing a color display test; and executing a light-emitting diode test.

A said performance check may comprise validating an operation of a system health protection component of the medical device, the system health protection component configured to respond to an unexpected condition. At least one of the user device and the medical device may be configured to generate the unexpected condition.

The system health protection component comprises a transient current detector, in which case, the method may comprise generating an unexpected condition; determining whether the transient current detector recognized the unexpected condition; and displaying one or more results of the performance check to the user via the user interface.

The system health protection component may additionally or alternatively comprise a thermal cutout. In this case, the method may comprise supplying power to a heating element; and determining whether the thermal cutout tripped in response to supplying power to the heating element. The method may further comprise resetting the thermal cutout in response to the thermal cutout being tripped; resupplying power to the heating element; determining whether the thermal cutout reset; and displaying one or more results of the performance check to the user via the user interface. Alternatively, the method may comprise determining whether the thermal cutout failed to trip; and displaying one or more results of the performance check to the user via the user interface in response to the thermal cutout failing to trip.

The method may comprise using the received status information to determine a status of a component of the medical device; and determining whether the component is in need of replacement based upon the determined status.

The status of the component may comprise a remaining operational life of the component. In this case, determining whether the component is in need of replacement may comprise determining if the remaining operational life of the component is under a threshold value.

The method may comprise determining whether the medical device is associated with an account information. The method may comprise prompting the user to order a replacement component for the medical device in response to a determination that the component is in need of replacement and/or automatically initiating an order for a replacement component for the medical device in response to a determination that the component is in need of replacement. Automatically initiating an order for a replacement component for the medical device may comprise generating a user interface information to cause one or more user interface elements to be displayed by a user interface of a second user device associated with a second user, the one or more user interface elements prompting the second user to confirm the order.

The action may comprise the user to input one or more parameters at the user interface of the user device, the one or more parameters being used to perform one or more diagnostic procedures on the medical device.

The user device may be remote from the medical device.

The method may comprise executing multiple maintenance tasks in sequence, multiple maintenance tasks in synchrony, or any combination thereof.

For purposes of summarizing the disclosed systems and apparatus, certain aspects, advantages and novel features of the disclosed systems and apparatus have been described herein. It is to be understood that not necessarily all such advantages may be achieved in accordance with any particular embodiment of the disclosed systems and apparatus. Thus, the disclosed systems and apparatus may be embodied or carried out in a manner that achieves or optimizes one advantage or group of advantages as taught herein without necessarily achieving other advantages as may be taught or suggested herein.

BRIEF DESCRIPTION OF THE DRAWINGS

These and other features, aspects, and advantages of the present disclosure will be described with respect to the following figures, which are intended to illustrate and not to limit the preferred embodiments.

DETAILED DESCRIPTION

Figure 1:
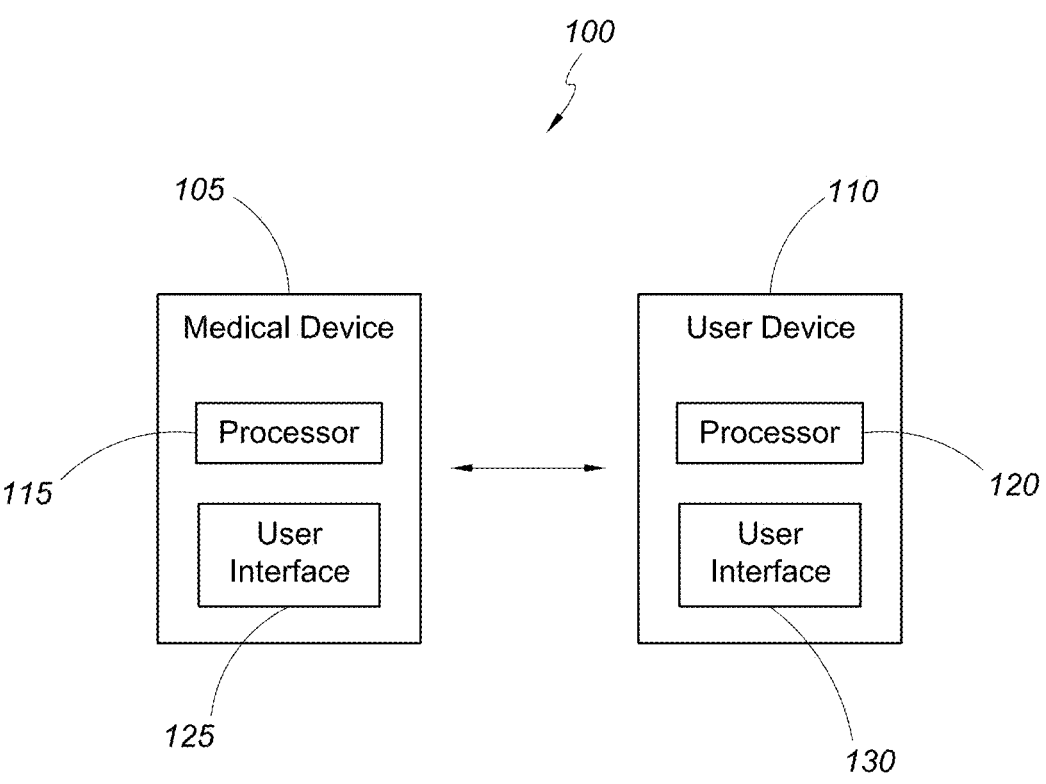
FIG. 1 shows an example block diagram of a maintenance system comprising a medical device and a user device.

FIG. 1 shows an example of a maintenance system 100 comprising a medical device 105 and a user device 110. The medical device 105 may comprise, for example but without limitation, a humidifier, a ventilator, a positive air pressure (PAP) device, a gases characteristic monitoring device, a high flow therapy device, or an insufflator. In particular the medical device is a humidifier that is configured to humidify respiratory gases prior to delivery to a patient. The humidifier is a non life supporting device, and is used as part of a respiratory humidification system, in conjunction with a ventilator and suitable medical tubing. The user device 110 may comprise, for example but without limitation, a computer, a mobile phone, a tablet, or any other consumer electronics device. The medical device 105 may communicate with the user device 110. In some embodiments, the medical device 105 may include a plurality of medical devices. In some embodiments, the user device 110 may include a plurality of user devices. The medical device 105 and the user device 110 each may include a processor 115 and a processor 120, respectively.

In some embodiments, one or more maintenance tasks associated with the maintenance system 100 may be executed on the user device 110 by the processor 120 as well as on the medical device 105 by the processor 115. In some embodiments, all of the maintenance tasks associated with the maintenance system 100 may be executed on the medical device 105 by the processor 115. In some such embodiments, the maintenance system 100 may not include the user device 110; the medical device 105 may include a user interface 125, and the medical device 105 may display information on the user interface 125. In other such embodiments, the maintenance system 100 may include the user device 110, the user device 110 may include a user interface 130, and the user device 110 may show information on the user interface 130.

Figure 2A:
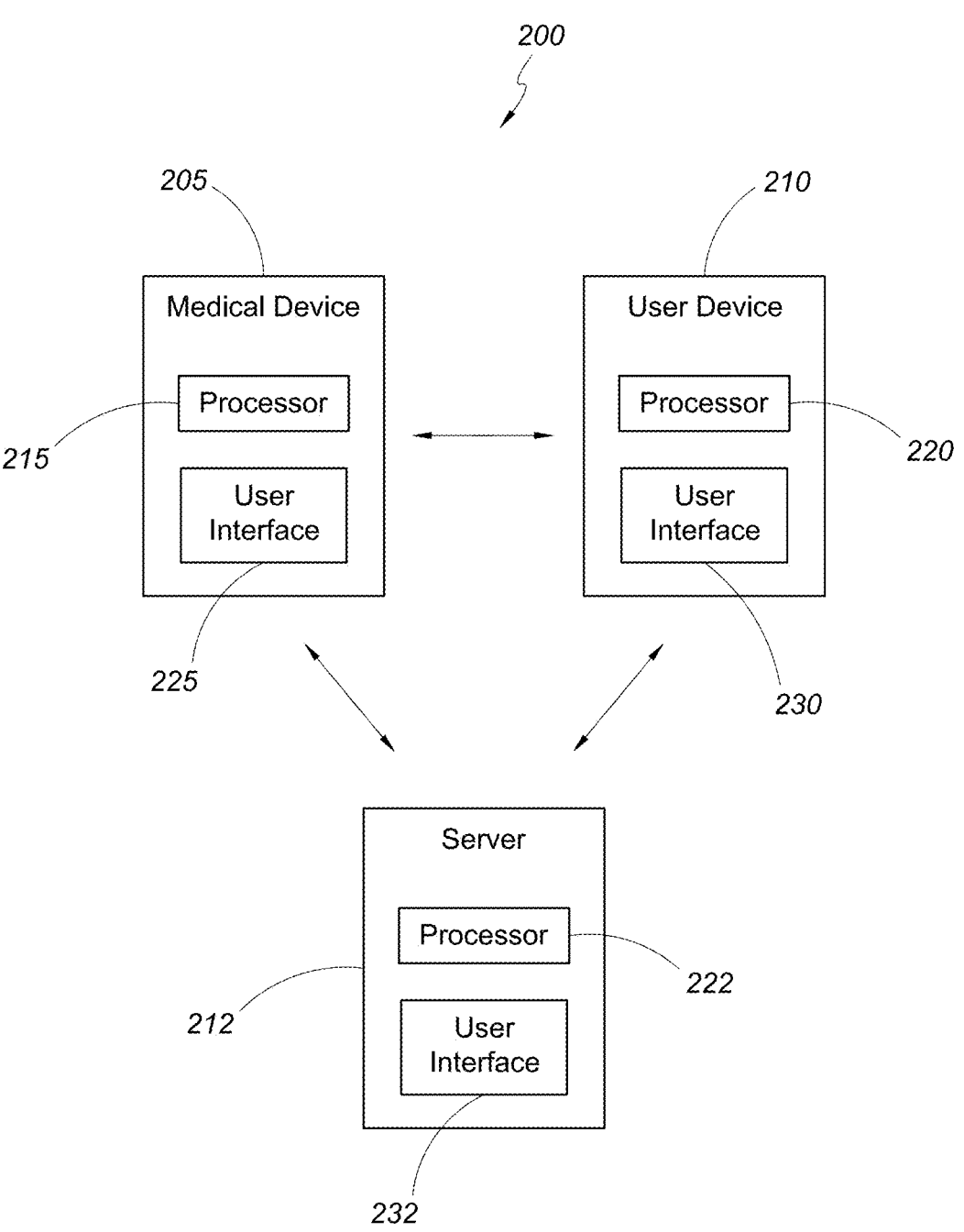
FIG. 2A shows an example block diagram of a maintenance system comprising a medical device, a user device, and a server.

A maintenance system for a medical device may also include a server. FIG. 2A shows an example of a maintenance system 200 comprising a medical device 205, a user device 210, and a server 212. The medical device 205 may communicate with one or both of the user device 210 and the server 212. The server 212 may communicate with the medical device 205 and/or the user device 210 through a direct connection, through a local area network, or through a wide area network such as the Internet. The medical device 205 and/or the user device 210 can send information to the server 212, or the server 212 can retrieve information from the medical device 205 and/or the user device 210. In some embodiments, each of the medical device 205, the user device 210, and the server 212 may communicate with any or all of the other two of the medical device 205, the user device 210, and the server 212.

In some embodiments, the medical device 205 may include a plurality of medical devices. In some embodiments, the user device 210 may include a plurality of user devices. In some embodiments, the server 212 may include a plurality of servers. In some embodiments, the maintenance system 200 includes at least one server 212, at least one medical device 205, and at least one user device 210. The medical device 205, the user device 210, and the server 212 each may include a processor 215, a processor 220, and a processor 222, respectively. The medical device 205 and the user device 210 each may include a user interface 225 and a user interface 230, respectively. In some embodiments, the server 212 may include a user interface 232.

In some embodiments, one or more maintenance tasks may be executed on the user device 210 by the processor 220 and/or on the server 212 by the processor 222. In some embodiments, one or more maintenance tasks may be executed on the medical device 205 by the processor 215. In some embodiments, the server 212 can undertake one or more of the functions of the user device 210. The server 212 may store data locally or in an external data store such as, without limitation, a database. In some embodiments, the medical device 205 and/or the user device 210 may send a result of a maintenance task, or additional information relevant to the maintenance task, to the server 212. In some embodiments, the server 212 may retrieve a result of a maintenance task, or additional information relevant to the maintenance task, from the medical device 205 and/or from the user device 210.

In some embodiments, one or more maintenance tasks disclosed herein may be executed on a medical device 105, 205 without the use of the user device 110, 210 or the server 212. The medical device 105, 205 may include executable instructions that permit a user to interact directly with the medical device 105, 205 and execute one or more maintenance tasks via the user interface 125, 225 located on the medical device 105, 205. In some embodiments, the medical device 105, 205 may compile the results of one or more maintenance tasks into a report. This report may include information obtained by the processor 115, 215 during execution of the maintenance task, or from a storage device associated with the medical device 105, 205. This information may include the name of a user who initiated the test and any notes the user may have entered via, for example, the user interface 125, 225. In some embodiments, the report may include a graph showing information obtained by the processor 115, 215 during the maintenance task. The report may include a history of alarms for the medical device 105, 205. The report may include information relating to the status of the medical device 105, 205 or of components associated with the medical device 105, 205. The report may be saved on a storage device associated with the medical device 105, 205 and later retrieved from the storage device. In some embodiments, the processor 115, 215 may send the report to a printer to be printed. In some embodiments the report may be displayed on the user interface 125, 225. In some embodiments the report may be accessed from the server 212 as an electronic report. In some embodiments the report may be emailed or texted or transmitted to the user in an appropriate electronic format.

Each of one or more maintenance tasks associated with the maintenance system 100, 200 may include a series of acts. In some such embodiments, one or more of the series of acts for each of the one or more maintenance tasks may be executed on the medical device 105, 205 by the processor 115, 215 and/or on the user device 110, 210 by the processor 120, 220. In some such embodiments, one or more of the series of acts for each of the one or more maintenance tasks may be executed on the server 212 by the processor 222.

Acts for maintenance tasks associated with the maintenance system 100, 200 can be executed concurrently or sequentially on any or all of the medical device 105, 205, the user device 110, 210, and/or the server 212. In some embodiments, the acts can be synchronized between the medical device 105, 205 and the user device 110, 210. In some embodiments, the acts can be synchronized between the medical device 205, the user device 210, and/or the server 212. For example, a maintenance task may include a series of acts and some of the series of acts may be executed on the medical device 205 and others of the series of acts may be executed on the user device 210 or the server 212. In some embodiments, execution of one or more maintenance tasks, or one or more of a series of acts for one or more maintenance tasks, on the user device 110, 210 by the processor 120, 220 may reduce the computational load on the processor 115, 215 of the medical device 105, 205. In some embodiments, execution of one or more maintenance tasks, or one or more of a series of acts for one or more maintenance tasks, on the user device 210 by the processor 220 and/or on the server 212 by the processor 222 may reduce the computational load on the processor 215 of the medical device 205. Such an arrangement may also extend the capability of the maintenance system 100, 200, as it may be easier to add functionality to the user device 110, 210 or to the server 212, such as for example, updating or upgrading software or replacing hardware, than to make changes to the medical device 105, 205.

The medical device 105, 205, the user device 110, 210, and/or the server 212 may communicate with each other via connections that include wired connections, wireless connections, combinations of wired and wireless connections, and/or connections based on any other suitable technology. In some embodiments, one or more of the connections may include a serial cable, for example but not limited to a universal serial bus (USB) cable. In some embodiments, one or more of the connections may include a wireless connection, for example but not limited to a cellular (for example, Global System for Mobile Communications or GSM), Bluetooth, or Wi-Fi connection. A wireless connection may be provided by technology (for example, a chip or chipset) integrated into one or more of the medical device 105, 205, the user device 110, 210, or the server 212. In some embodiments, a wireless chip or chip set may be built into one or more of the medical device 105, 205, the user device 110, 210, or the server 212. A wireless connection may be provided by an external device (for example, a "dongle" or other such device connectible via, for example, a USB port) connected to one or more of the medical device 105, 205, the user device 110, 210, or the server 212. One skilled in the art would appreciate that other implementations of wireless connections are possible.

One or more of the user interfaces 125, 225, 130, 230, 232 may be used by a user to perform actions, including but not limited to controlling the maintenance system 100, 200, providing information to the maintenance system 100, 200, and receiving information from the maintenance system 100, 200 regarding results of any maintenance tests or checks. One or more of the processors 115, 215, 120, 220, 222 may execute user interface software comprising instructions that cause information to be displayed on, or retrieved from, the user interface 125, 225, 130, 230, 232, respectively. One or more of the processors 115, 215, 120, 220, 222 may execute user interface software to cause at least one screen to be displayed on one or more of the user interfaces 125, 225, 130, 230, 232. In some embodiments, the at least one screen may be generated by the processor 222 of the server 212, and the processor 220 of the user device 210 and/or the processor 215 of the medical device 205 may retrieve the at least one screen from the server 212 and then display the at least one screen to the user on the user interface 225 or the user interface 230. In some embodiments, the at least one screen may be generated by the processor 115, 215 of the medical device 105, 205, and the processor 220 of the user device 210 may retrieve the at least one screen from the medical device 105, 205 and may then display the at least one screen to the user on the user interface 125, 225. In some embodiments, the processor 120, 220 of the user device 110, 210 may both generate and display the at least one screen. In some embodiments, the at least one screen may include a web page.

A user may be able to remotely view status information about the medical device 105, 205 on the user interface 130, 230, 232 of the user device 110, 210 or the server 212, respectively. As a result, a user is not required to be physically located near the medical device 105, 205 to access status information of the medical device 105, 205. This is particularly useful when the maintenance system 100, 200 comprises more than one medical device 105, 205, as a user can view status information of the more than one medical device 105, 205 at the same time. For example the user interface 130, 230 may be configured to provide a multi pane view, wherein each pane on the user interface 130, 230 displays the status of a particular medical device 105, 205. The processor 120, 220 may execute appropriate user interface software to generate the multi pane view on the user interface 130, 230 respectively.

Figure 2B:
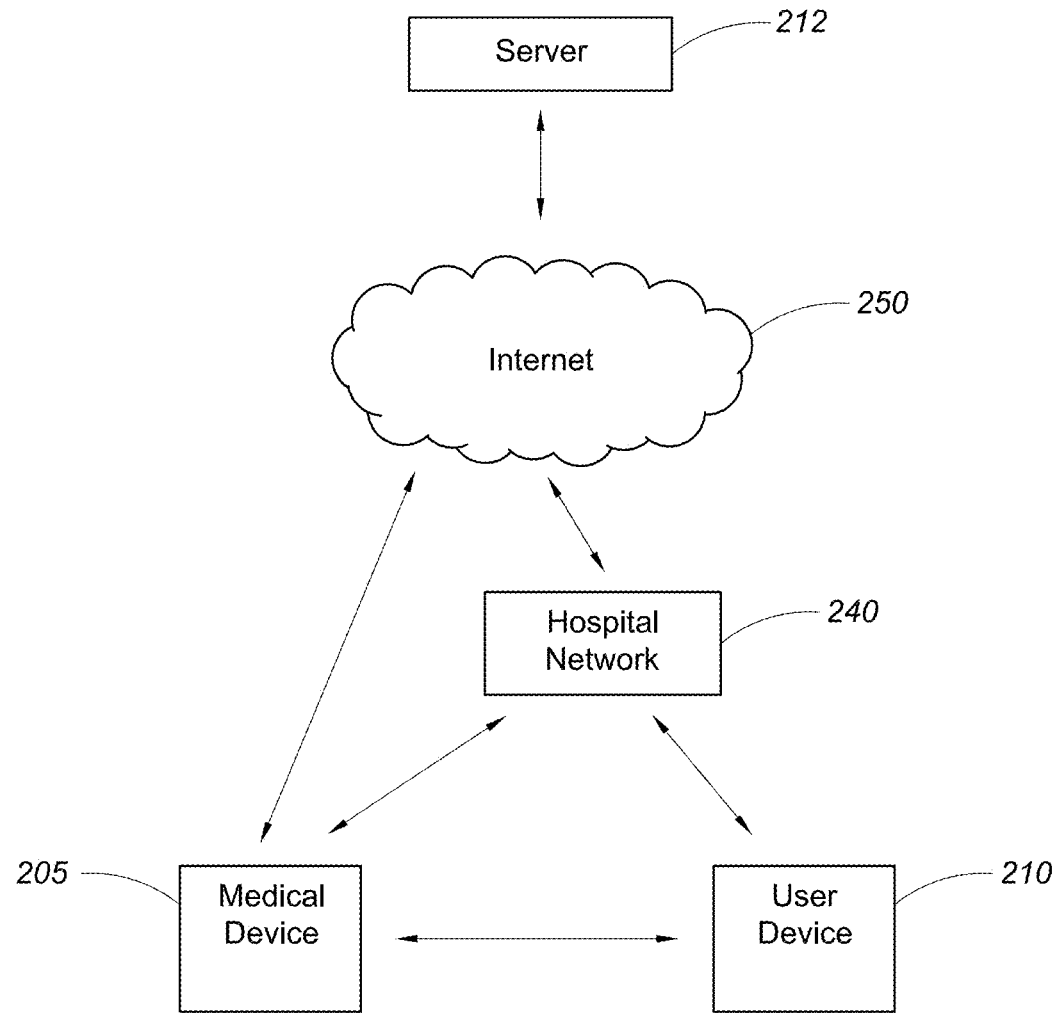
FIG. 2B shows another example block diagram of a maintenance system comprising a medical device, a user device, and a server.

For instance, FIG. 2B shows an example of the maintenance system 200 wherein the medical device 205, the user device 210, and the server 212 communicate through various different local and wide area connections. The medical device 205 and the user device 210 may be local to each other and communicate through a direct connection (for example, through a serial cable such as a USB cable, a wireless connection such as Bluetooth, and/or the like) or through a local area network such as a hospital network 240. In some embodiments, the medical device 205 and/or the user device 210 may be connected to the Internet 250, either directly or indirectly (for example, through the hospital network 240). In addition, the server 212 may be located remotely from the hospital and communicate with the hospital network 240, the medical device 205, and/or the user device 210 through the Internet 250. As such, a user may be able to view status information for the medical device 205 locally through the user interface 130 of the user device 210, or remotely through the user interface 232 of the server 212. In some embodiments, a remote user at the server 212 may need to be authenticated (for example, through the hospital network 240) before being able to access and communicate with the medical device 205 and/or the user device 210.

In some embodiments, a user may need to perform one or more authentication procedures to access the user interface 125, 225, 130, 230, 232. The one or more authentication procedures may be determined by authentication software executed by one or more of the processors 115, 215, 120, 220, 222. The one or more authentication procedures may involve interaction by a user with one or more of the medical device 105, 205, the user device 110, 210, or the server 212 using a physical dongle, an RFID tag, a biometric scanner, a keypad for entering a password or passcode, or any other suitable authentication technology.

Figure 2C:
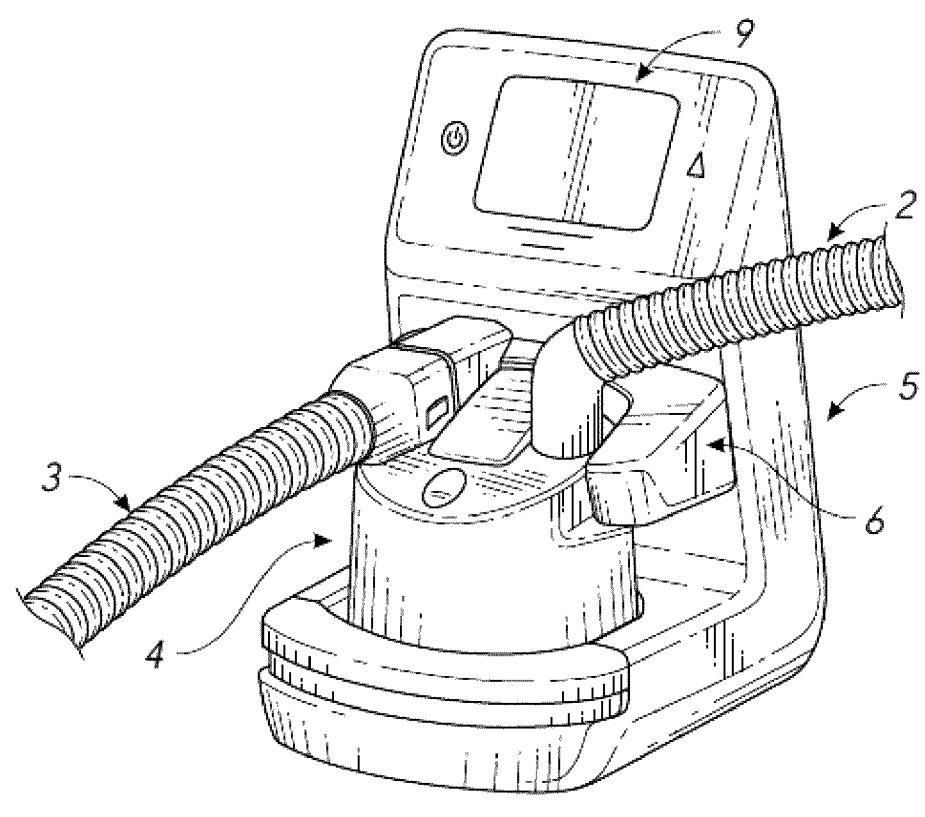
FIG. 2C shows a view of an example medical device.

As an example of the medical device 105, 205, FIG. 2C shows a respiratory humidifier 5. As an example of the user interface 125, 225 of the medical device 105, 205, the respiratory humidifier 5 includes a user interface 9. In the present disclosure the medical device as referred to may also refer to the respiratory humidifier 5, and the user interface may also refer to the interface 9 on the respiratory humidifier 5. The user interface 9 is an example of the user interface 125, 225. In one configuration the user interface 9 is a touch screen that allows a user to input information or commands by touching the screen with the user's finger or a suitable stylus. Alternatively the user interface 9 may include a set of buttons or knobs or other suitable actuation elements that can be actuated by the user to input information or commands. The respiratory humidifier 5 also includes a coupleable component or a removabley component. In the illustrated configuration of FIG. 2C the coupleable component is a sensor cartridge 6. The sensor cartridge 6 includes one or more integrated sensors. The sensors may be temperature sensors or flow sensors or a combination of temperature and flow sensors. The one or more sensors may be inserted into a gases flow path such. For example the sensors may be inserted into the inspiratory limb 3, or into the humidification chamber 4. In one exemplary configuration the sensor cartridge comprises at least a temperature sensor that aligns with or is inserted into an inlet port of the humidification chamber 4, and the sensor cartridge further comprising at least a temperature sensor and a flow sensor that aligns with or is inserted into an outlet port of the humidification chamber 4. An expiratory limb 2, an inspiratory limb 3, and a humidification chamber 4 may be removably attached to the respiratory humidifier 5 in preparation for or while providing therapy to a patient. As described above, in some embodiments one or more maintenance tasks may be executed on the respiratory humidifier 5 in cooperation with the user device 210 and/or the server 212. In some embodiments, one or more maintenance tasks may be executed by the respiratory humidifier 5 without the user of the user device 110, 210 or the server 212. In some embodiments, the user can interact with the user interface 9 to cause the respiratory humidifier 5 to perform one or more maintenance tasks. The respiratory humidifier 5 may also comprise a chip or chip sets to allow wireless communication with the server 212 and/or the user 210. The respiratory humidifier 5 includes suitable electronics hardware and a processor and a memory unit. The maintenance tasks may be stored as a executable software on the memory unit, and the processor being configured to execute the software to cause the respiratory humidifier 5 to perform one or more maintenance tasks. The respiratory humidifier 5 may be configured to generate a report of the maintenance tasks performed and the results of the maintenance tasks. The respiratory humidifier 5 may transmit the report to the user device 110, 210 or to the server 212. Alternatively the respiratory humidifier 5 may transmit the generated report to a printer, such as for example a printer within a hospital via the hospital network. In a further configuration the sensor cartridge 6 may include at least a memory unit and may further include a processor that is configured to cause the respiratory humidifier 5 to perform one or more maintenance tasks.

One or more of the user interfaces 125, 225, 130, 230, 232, 9 may also display status information of the medical device 105, 205. Status information about the medical device 105, 205 may include at least one of a model number, a serial number, or a software version related to the medical device 105, 205, 5; the remaining lifetime of a consumable component associated with the medical device 105, 205; the time elapsed since the last maintenance check of the medical device 105, 205; a history of alarms for the medical device 105, 205; and an operational state of the medical device 105, 205, for example whether or not the medical device 105, 205 is currently being used to provide therapy to a patient. For example, the user interface 9 may display status information about the respiratory humidifier 5, including, among other information as previously described, the remaining lifetime of the sensor cartridge 6. In some embodiments, the status information displayed on the one or more of the user interfaces 125, 225, 130, 230, 232 may also be recorded by the processor 115, 215, 120, 220, 222 on a storage device associated with the medical device 105, 205, the user device 110, 210, or the server 212 after the user device 110, 210 is disconnected from the medical device 105, 205.

A maintenance task associated with the maintenance system 100, 200 may include a maintenance check, including but not limited to at least one of an electrical safety check, a physical check, a functional check, or a performance check. A maintenance check may be executed on a regular or semi-regular basis or at the discretion of a user. A maintenance check may be undertaken annually, bi-annually, weekly or at any other frequency. In some embodiments, an execution frequency of a maintenance check may be defined by a user. In some embodiments, an execution frequency of a maintenance check may be pre-defined, for example, during manufacture or configuration of the medical device 105, 205, the user device 110, 210, or the server 212. In some embodiments, a maintenance check may be executed at a discrete time set by the user.

In some embodiments, the processor 115, 215, 120, 220, 222 may record results of maintenance tasks associated with the maintenance system 100, 200 on a storage device associated with the medical device 105, 205, the user device 110, 210, or the server 212. In some embodiments, the processor 115, 215, 120, 220, 222 may use the recorded results to determine when to display a reminder on the user interface 125, 225, 130, 230, 232 to remind a user that a maintenance task is due. The reminder may provide a user with an option to initiate the maintenance task by, for example, providing input via the user interface 125, 225, 130, 230, 232. In some embodiments, the processor 115, 215, 120, 220, 222 may automatically initiate the maintenance task. The processor 115, 215, 120, 220, 222 may initiate the maintenance task during a start-up sequence of the medical device 105, 205. In some embodiments, the processor 115, 215, 120, 220, 222 may use an operational state of the medical device 105, 205 to determine whether to initiate the maintenance task. For example, the processor 115, 215, 120, 220, 222 may wait until the medical device 105, 205 is in a standby or sleep state—such as when the medical device 105, 205 is not providing therapy to a patient—to initiate the maintenance check. The processor 115, 215, 120, 220, 222 may display a message on the user interface 125, 225, 130, 230, 232 instructing a user to confirm that the medical device 105, 205 is not providing therapy to a patient before the maintenance task is initiated.

In some embodiments, the processor 115, 215, 120, 220, 222 may compile the results of one or more maintenance tasks associated with the maintenance system 100, 200 into a report. This report may include information obtained by the processor 115, 215, 120, 220, 222 during execution of the maintenance task, or from a storage device associated with the medical device 105, 205, the user device 110, 210, or the server 212. This information may include the name of a user who initiated the test and any notes the user may have entered via, for example, the user interface 125, 225, 130, 230, 232. In some embodiments, the report may include a graph showing information obtained by the processor 115, 215, 120, 220, 222 during the maintenance task. The report may include a history of alarms for the medical device 105, 205. The report may be saved on a storage device associated with the medical device 105, 205, with the user device 110, 210, or with the server 212 and later retrieved from the storage device. In some embodiments, the processor 115, 215, 120, 220, 222 may send the report to a printer to be printed. In some embodiments the report may be displayed on the user interface 125, 225, 130, 230, 232.

In some embodiments, a maintenance task may include user interaction. A maintenance task may include an act wherein the processor 115, 215, 120, 220, 222 displays a message on the user interface 125, 225, 130, 230, 232 requesting a user to take an action or provide information needed for the maintenance task. A maintenance task may include an act wherein the processor 115, 215, 120, 220, 222 allows a user to enter notes via the user interface 125, 225, 130, 230, 232. Such notes may be included in a report. In some embodiments, a maintenance task may not require user interaction. The processor 115, 215, 120, 220, 222 may execute such a maintenance task autonomously.

A maintenance task may include one or more entry conditions and one or more exit conditions. In some embodiments, the processor 115, 215, 120, 220, 222 may be able to automatically detect an entry condition or an exit condition. In some embodiments, the processor 115, 215, 120, 220, 222 may need to be informed of an entry condition or an exit condition by user input via, for example, the user interface 125, 225, 130, 230, 232. An entry condition may be an event or state upon which the commencement of a maintenance task is contingent. For example, an entry condition may include the engagement of an electrical and/or pneumatic connector, the engagement of a coupleable component, or the cooling to a predetermined temperature of a heating element of the medical device 105, 205. In some embodiments, the processor 115, 215, 120, 220, 222 may display a message on the user interface 125, 225, 130, 230, 232 instructing a user to take an action that will cause an entry condition to be satisfied. For example, the processor 115, 215, 120, 220, 222 may display a message on the user interface 125, 225, 130, 230, 232 instructing a user to engage a coupleable component with the medical device 105, 205. An exit condition may be an event or state which, at least temporarily, causes a maintenance task to cease. For example, an exit condition may include the disengagement of an electrical and/or pneumatic connector, the disengagement of a coupleable component, the detection of an alarm, or the loss of a data connection between at least two of the medical device 105, 205, the user device 110, 210, and the server 212.

An electrical safety check may include validation of correct and safe operation of one or more electrical components of the medical device 105, 205. An electrical safety check may have requirements specific to the operating locale of the medical device 105, 205. For example, local or national laws or regulations may include differing electrical safety requirements. In some embodiments, an electrical safety check may include an act wherein the processor 115, 215, 120, 220, 222 displays a message on the user interface 125, 225, 130, 230, 232 instructing a user to perform one or more acts of the electrical safety check as specified by local or national laws or regulations. An electrical safety check may include an act wherein the processor 115, 215, 120, 220, 222 displays a message on the user interface 125, 225, 130, 230, 232 instructing a user to input a result of the one or more acts of the electrical safety check performed by the user. The user may be instructed to indicate success or failure, provide measurements, or otherwise describe the result. An electrical safety check may include an act wherein the processor 115, 215, 120, 220, 222 displays an image and/or an animation on the user interface 125, 225, 130, 230, 232 showing how to connect a probe of an electrical safety tester to the medical device 105, 205 to perform an electrical safety test. The user interface 125, 225, 130, 230, 232 may also display a caution to the user indicating areas where the safety tester probe is not to be connected.

Figure 3:
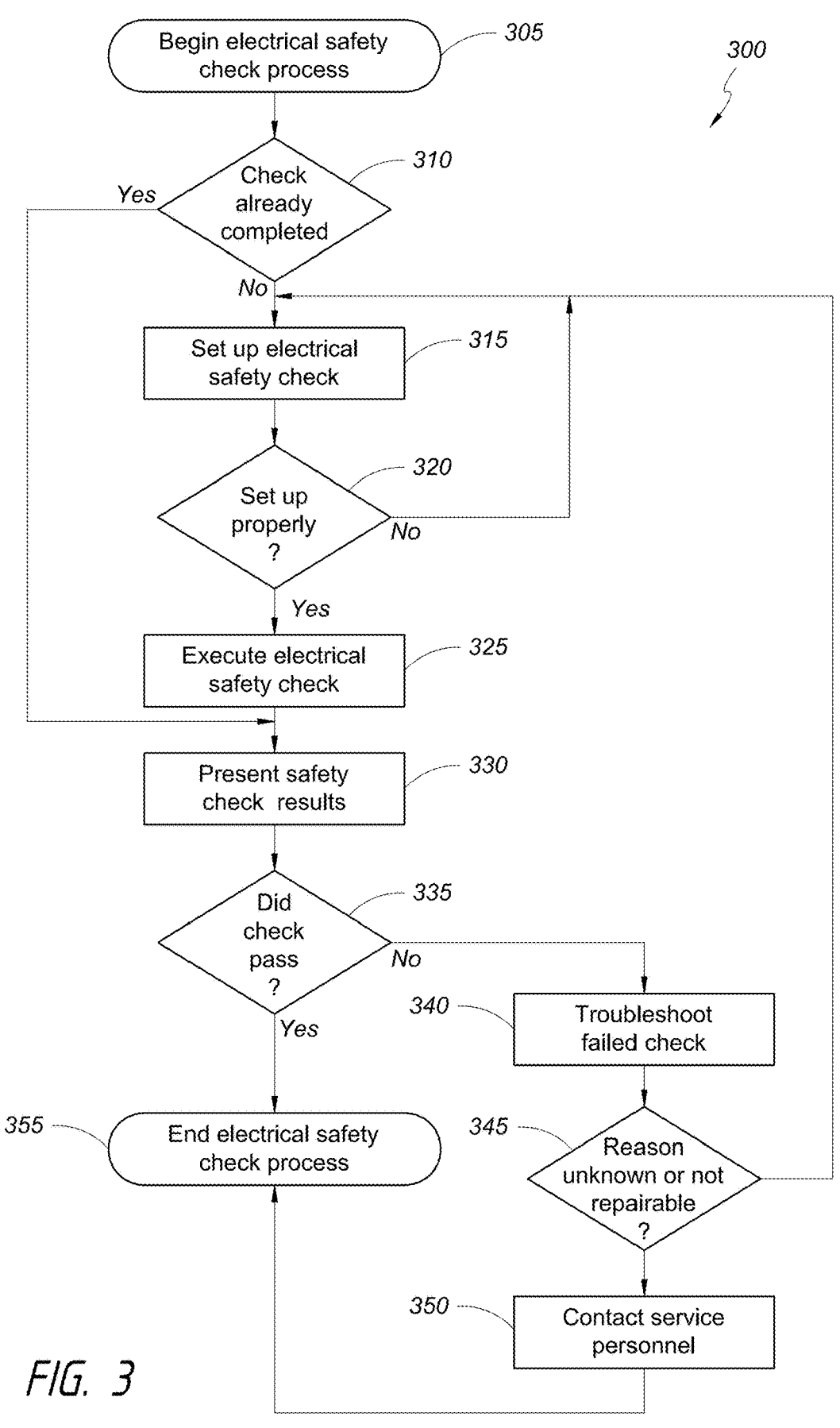
FIG. 3 shows an example flowchart of a method for executing an electrical safety check of a medical device.

FIG. 3 is a process 300 for executing an electrical safety check of a heater base used by the medical device 105, 205 according to an embodiment of the present disclosure. At block 305 the process 300 begins. In some embodiments, an electrical safety check is recommended or required to be performed on a periodic basis, such as for example, annually. Accordingly, at block 310 the process 300 determines whether a recent (periodically required) safety check of the medical device 105, 205 has already been performed. In some embodiments, an inquiry may be presented to the user, who may be a maintenance technician, via the user interface 125, 225, 130, 230, 232, and the user may input a response to the inquiry via the user interface 125, 225, 130, 230, 232 as well. If the user indicates, or the process 300 otherwise determines that the periodically required safety check of the medical device 105, 205 has been completed, the process 300 advances to block 330, where results of the safety check are presented.

If the user indicates, or the process 300 otherwise determines that the periodically required safety check of the medical device 105, 205 has not been completed, then the process 300 advances to block 315, where the user is prompted to set up the electrical safety check. In some embodiments, the electrical safety check requires the use of an external electrical safety tester having one or more probes. Illustratively, by way of non-limiting example, such a probe may be placed in electrical communication with the heater plate of the medical device 105, 205 to be used to test the electrical safety of the heater plate operation. The electrical safety tester may be provided by the user, who may be a maintenance technician trained and equipped to conduct such tests. In some embodiments, the user interface 125, 225, 130, 230, 232 displays instructions on how to connect or attach the one or more probes of the electrical safety tester to the medical device 105, 205. In some embodiments, the user interface provides reference and/or access to country-specific or region-specific standards or regulations that apply to electrical safety checks of the medical device 105, 205 being checked. In some embodiments, the user interface 125, 225, 130, 230, 232 displays a message, including for example, a modal message. As described previously the message may be displayed on the user interface 9. The modal message can include, such as for example, a pop-up window, to disconnect certain connections to the medical device 105, 205. For example, the modal message may request the user to disconnect a USB null modem cable connected to medical device 105, 205 before executing the electrical safety check. The modal message may instruct to user to ensure that the user device 110, 210 is also disconnected from the medical device 105, 205 when the electrical safety check is performed. Such disconnection may be required to avoid damaging components of or in communication with the medical device 105, 205 during the electrical safety check.

At block 320, the process 300 determines whether the electrical safety check is set up properly. In some embodiments, the determination is made by receiving input from the user. In some embodiments, one or more of the processors 115, 215, 120, 220, 222 may determine whether the safety check set up is complete. If the process 300 determines that the electrical safety check set up is not complete, then the process returns to block 315 to prompt the user to set up the electrical safety check. In some embodiments, the user interface 125, 225, 130, 230, 232 may provide a plurality of instructions and/or troubleshooting guides to assist the user in setting up the electrical system check. Once the process 300 determines that the electrical safety check is set up properly, the process 300 advances.

At block 325, the electrical safety check is executed. In some embodiments, the processor 115, 215 controls the electrical circuitry of the medical device 105, 205 to perform one or more acts that exercise the electrical functionality of the medical device 105, 2015. In some embodiments, the user may be prompted to provide input as requested by the external electrical safety tester and/or the user interface 125, 225, 130, 230, 232.

At block 330, the results of the electrical safety check are presented via the user interface 125, 225, 130, 230, 232. In some embodiments, the results may be stored in a memory device that may be located in the medical device 105, 205, in the user device 110, 210, in the server 212, or in an external memory device.

At block 335, the process 300 determines whether the executed electrical safety check has passed. If the electrical safety check passes, then the process 300 ends at block 355. If the electrical safety check fails, then the process 300 advances to block 340, where the process 300 presents, via the user interface 125, 225, 130, 230, 232, troubleshooting suggestions for determining the cause of the electrical safety check failure. In some embodiments, the user interface 125, 225, 130, 230, 232 displays a series of suggestions for the user to explore, and after each suggestion, the user may provide a response indicating whether or not that particular suggestion identified the reason for the electrical check failure. At block 345, the process 300 determines whether the reason for failure of the electrical safety check is understood or repairable. If it is, the process 300 returns to block 310 to restart the electrical safety check. If at block 345, the process 300 determines that the reason for failure of the electrical safety check is not known or cannot be repaired, the process 300 advances to block 350, where a manufacturer service representative is contacted to identify the source of the failure.

If performance of the electrical safety check according to process 300 is interrupted, a message, such as a modal message, may be displayed to the user indicating an interruption has occurred. In some embodiments, if the electrical safety check is re-established, the electrical safety check may continue from the point at which the interruption occurred. In some embodiments, the electrical safety check may start over at block 305.

Performance of the electrical safety check is not limited to the order and number of steps described in the process 300. While the electrical safety check according to the process 300 describes the execution of a series of steps in a particular sequence, the individual steps may be performed in any order, unless otherwise specified. Additionally, performance of the electrical safety check does not require execution of all the steps described in the process 300. In some embodiments, the electrical safety check may include additional steps not described in the process 300. In some embodiments, the electrical safety check may not include all steps described in the process 300. One or more steps of the process 300 may be executed by any one of or any combination of the processors 115, 215, 120, 220, 222 or other processors residing in the same devices or other devices.

A physical check may include validation of correct and safe operation of one or more physical aspects of the medical device 105, 205. In some embodiments, a physical check may include an act wherein the processor 115, 215, 120, 220, 222 displays one or more messages on the user interface 125, 225, 130, 230, 232 instructing a user to look for physical defects or other issues in or on the medical device 105, 205. In another example the message may be displayed on the touch screen 9 of the respiratory humidifier 5. The message may instruct the user to conduct an external inspection of the medical device 105, 205. The message may in the form of animations. In some embodiments, the message may instruct the user to at least partially remove one or more components and/or housing panels to access internal areas of the medical device 105, 205. A physical check may include an act wherein the processor 115, 215, 120, 220, 222 displays one or more messages on the user interface 125, 225, 130, 230, 232 instructing a user to input a result or description of the one or more acts of the physical check performed by the user. The user may be instructed to indicate success or failure, provide measurements, or otherwise describe the physical check. In some embodiments, the user input indicates whether the physical condition of the aspect being checked is in acceptable or unacceptable condition. In some embodiments, the user interface 125, 225, 130, 230, 232 provides guidance on what to check for regarding physical damage to the medical device 105, 205. For example, the user interface 125, 225, 130, 230, 232 may ask if the user has have already performed the checks by following the instructions in the patient manual. If so, the application will ask for the results. In some embodiments, checkboxes may be provided on the user interface 125, 225, 130, 230, 232 to allow the user to enter the results of the physical inspections. If the user has not completed the physical check already, then the application will provide instructions that guide the user through checking various physical aspects of the medical device 105, 205. In some embodiments, the user device 110, 210 or the server 212 does not interact with the medical device 105, 205 to perform the physical check; instead, the user is prompted on the user interface 125, 225, 130, 230, 232 to inspect and assess the physical condition of the medical device 105, 205. In some embodiments, pass/fail buttons or equivalents thereof are provided to the user to enter the status of the physical characteristics being assessed by the user. In some embodiments, a text panel is provided to permit the user to enter comments about the status of the physical characteristics of the medical device 105, 205 being checked. In an further alternative embodiment the medical device 105, 205 may be configured to perform a part or all of the physical check by checking for appropriate conditions such as for example whether a chamber is correctly connected, whether an inspiratory limb 3 is correctly connected, whether an expiratory limb is correctly connected and so on.

Figure 4:
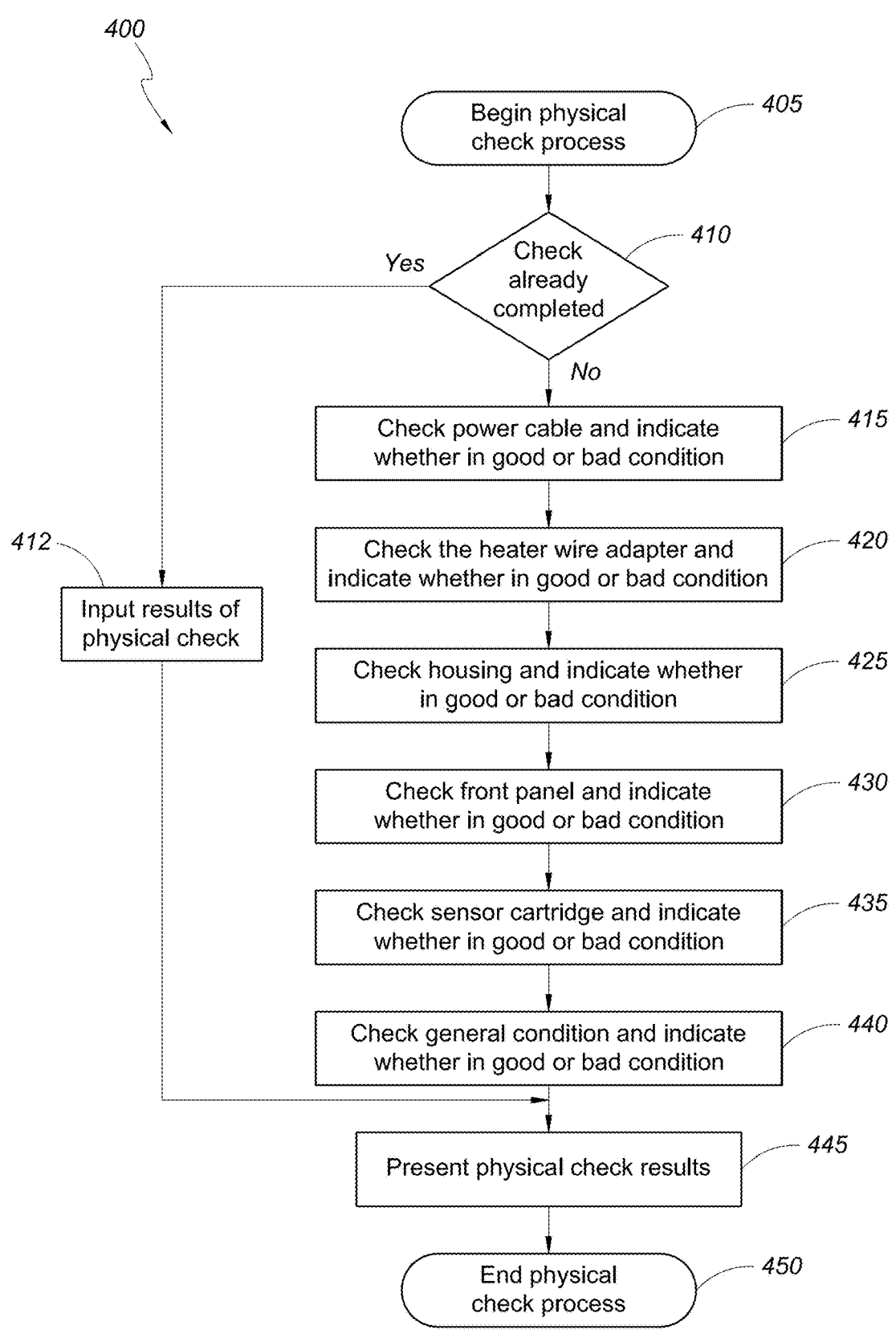
FIG. 4 shows an example flowchart of a method for executing a physical check of a medical device.

FIG. 4 is a process flow diagram of a process 400 for executing a physical check of the medical device 105, 205 according to an embodiment of the present disclosure. At block 405, the process 400 begins. In some embodiments, a physical check is recommended or required to be performed on a periodic basis, such as for example, annually. In some embodiments, the maintenance system 100, 200 provides guided instructions for the user to follow in performing the physical check of the medical device 105, 205. It is possible that the user, such as for example, a maintenance technician, does not need to use the provided guided instructions based on, for example, training and/or experience in performing such physical checks of the medical device 105, 205.

Accordingly at block 410, the process 400 determines whether the physical check of the medical device 105, 205 has already been performed. In some embodiments, an inquiry may be presented to the user, who may be a maintenance technician, via the user interface 125, 225, 130, 230, 232, and the user may input a response to the inquiry via the user interface 125, 225, 130, 230, 232 as well. If the process 400 determines that the physical check has been performed, then the process 400 advances to block 412, where the user is prompted to input the results of the various physical checks performed on the medical device 105, 205. In some embodiments, the user interface 125, 225, 130, 230, 232 presents a set of graphical control elements, such as option buttons or radio buttons, for the user to select whether each of the performed physical checks passed or failed. Once the results of the physical check are input, the process 400 advances to block 445, where the results are presented to the user. In some embodiments, the results may be stored in a memory storage device that may be located in the medical device 105, 205, in the user device 110, 210, in the server 212, or in an external memory storage device.

If the user indicates, or the process 400 otherwise determines, that the physical check of the medical device 105, 205 has not been completed, then the process 400 advances to block 415, where the user is prompted to inspect the physical condition of a power cable used to supply outlet power to the medical device 105, 205. In some embodiments, the user interface 125, 225, 130, 230, 232 may provide images, animations, video presentations, audio presentations, text, combinations thereof, and the like to provide instructional guidance to the user on how to inspect the physical condition of the power cable. Illustratively, by way of non-limiting example, the user interface 125, 225, 130, 230, 232 may provide an animation illustrating how to access, secure, and inspect the power cable. The user is also prompted to indicate whether or not the physical condition of the power cable is acceptable. The user interface 125, 225, 130, 230, 232 may provide an input interface for the user to input the results of the physical check of the power cable. In some embodiments, such input may be provided by selecting a checkbox or radio button indicating whether the physical check of the power cord passed or failed. In some embodiments, the user interface 125, 225, 130, 230, 232 may provide for the input of text comments which may be used to further describe the condition of the inspected power cable. Once the physical inspection of the power cable is completed and user input is provided describing the assessed physical condition of the power cable, the user interface 125, 130, 232 prompts the user to proceed to a next physical check of the medical device 105, 205. In response to a request by the user to proceed to a next physical check, the process 400 advances to block 420.

At block 420, the user interface 125, 225, 130, 230, 232 prompts the user to inspect the physical condition of a heater wire adapter. The heater wire adapter may be used to physically connect and electrically communicate between the medical device 105, 205 and a heating wire or element configured to heat respiratory gases as the gases pass through, for example, an inspiratory conduit to the patient. As discussed above with respect to block 415, the user interface 125, 225, 130, 230, 232 may provide images, animations, video presentations, audio presentations, text, combinations thereof, and the like to present instructional guidance to the user on how to inspect the physical condition of the heater wire adapter. The user interface 125, 225, 130, 230, 232 may prompt the user to indicate whether or not the physical condition of the heater wire adapter is acceptable.

The user interface 125, 225, 130, 230, 232 may also provide an input interface for the user to input the results of the physical check of the heater wire adapter. Once the physical inspection of the heater wire adapter is completed and user input is provided describing the assessed physical condition of the heater wire adapter, the user interface 125, 130, 232 prompts the user to proceed to a next physical check of the medical device 105, 205. In response to a request by the user to proceed to a next physical check, the process 400 advances to block 425.

At block 425, the user interface 125, 225, 130, 230, 232 prompts the user to inspect the physical condition of a housing of the medical device 105, 205. The housing includes the external structure of the medical device 105, 205 which, among other things, serves to protect internal components of the medical device 105, 205 from the environment. Once again, as discussed above, the user interface 125, 225, 130, 230, 232 may provide images, animations, video presentations, audio presentations, text, combinations thereof, and the like to present instructional guidance to the user on how to inspect the physical condition of the housing. The user interface 125, 225, 130, 230, 232 may prompt the user to indicate whether or not the physical condition of the housing is acceptable. The user interface 125, 225, 130, 230, 232 may also provide an input interface for the user to input the results of the physical check of the housing. Once the physical inspection of the housing is completed and user input is provided describing the assessed physical condition of the housing, the user interface 125, 130, 232 prompts the user to proceed to a next physical check of the medical device 105, 205. In response to a request by the user to proceed to a next physical check, the process 400 advances to block 430.

At block 430, the user interface 125, 225, 130, 230, 232 prompts the user to inspect the physical condition of a front panel of the medical device 105, 205. The front panel may include the user interface 125, 225, 130, 230, 232, such as, by way of non-limiting example, a display, a dial, a switch, a plurality of physical buttons or keys, a plurality of virtual buttons or keys, a speaker, a microphone, and the like. The user interface 125, 225, 130, 230, 232 may provide images, animations, video presentations, audio presentations, text, combinations thereof, and the like to present instructional guidance to the user on how to inspect the physical condition of the front panel. The user interface 125, 225, 130, 230, 232 may also prompt the user to indicate whether or not the physical condition of the front panel is acceptable. The user interface 125, 225, 130, 230, 232 may also provide an input interface for the user to input the results of the physical check of the front panel. Once the physical inspection of the front panel is completed and user input is provided describing the assessed physical condition of the front panel, the user interface 125, 130, 232 prompts the user to proceed to a next physical check of the medical device 105, 205. In response to a request by the user to proceed to a next physical check, the process 400 advances to block 435.

At block 435, the user interface 125, 225, 130, 230, 232 prompts the user to inspect the physical condition of a sensor cartridge of the medical device 105, 205. In some embodiments, the sensor cartridge is mechanically and electrically connected to a heater base. The sensor cartridge may be a replaceable module that houses a number of sensors used to measure parameters of the medical device 105, 205 during operation and provide the measurements to the processor 115, 215 to control the operation of the medical device 105, 205. The sensor cartridge may be configured to provide for the transfer of power to the sensors while also provide mounting locations for the sensors within the medical device 105, 205. The sensor cartridge may also allow for the transfer of data between the sensors and the processor 115, 215 of the medical device 105, 205. The user interface 125, 225, 130, 230, 232 may provide images, animations, video presentations, audio presentations, text, combinations thereof, and the like to present instructional guidance to the user on how to inspect the physical condition of the front panel. The user interface 125, 225, 130, 230, 232 may also prompt the user to indicate whether or not the physical condition of the sensor cartridge is acceptable. The user interface 125, 225, 130, 230, 232 may also provide an input interface for the user to input the results of the physical check of the sensor cartridge. Once the physical inspection of the sensor cartridge is completed and user input is provided describing the assessed physical condition of the sensor cartridge, the user interface 125, 130, 232 prompts the user to proceed to a next physical check of the medical device 105, 205. In response to a request by the user to proceed to a next physical check, the process 400 advances to block 440.

At block 440, the user interface 125, 225, 130, 230, 232 prompts the user to inspect the general physical condition of the medical device 105, 205. This is an opportunity for the user to inspect the medical device 105, 205 for any other damage or excessive wear that may render the medical device 105, 205 inoperable or not suited for use. The user interface 125, 225, 130, 230, 232 may also prompt the user to indicate whether or not the general physical condition of the medical device 105, 205 is acceptable. The user interface 125, 225, 130, 230, 232 may provide images, animations, video presentations, audio presentations, text, combinations thereof, and the like to present instructional guidance to the user on how to inspect the physical condition of the front panel. The user interface 125, 225, 130, 230, 232 may also provide an input interface for the user to input the results of the physical check of the front panel. Once the physical inspection of the front panel is completed and user input is provided describing the assessed general physical condition of the medical device 105, 205, the user interface 125, 130, 232 prompts the user to proceed in the process 400.

At block 445, the results are presented to the user. In some embodiments, the results may be stored in a memory storage device that may be located in the medical device 105, 205, in the user device 110, 210, in the server 212, or in an external memory storage device. A skilled artisan will appreciate that other features, characteristics, or components of the medical device 105, 205 may also be included in the physical check without departing from the scope of the present disclosure.

If performance of the physical check according to process 400 is interrupted, a message, such as a modal message, may be displayed to the user indicating an interruption has occurred. In some embodiments, if the physical check is re-established, the physical check may continue from the point at which the interruption occurred. In some embodiments, the physical check may start over at block 405.

Performance of the physical check is not limited to the order and number of steps described in the process 400. While the physical check according to the process 400 describes the execution of a series of steps in a particular sequence, the individual steps may be performed in any order, unless otherwise specified. Additionally, performance of the physical check does not require execution of all the steps described in the process 400. In some embodiments, the physical check may include additional steps not described in the process 400. In some embodiments, the physical check may not include all steps described in the process 400. One or more steps of the process 400 may be executed by any one of or any combination of the processors 115, 215, 120, 220, 222 or other processors residing in the same devices or other devices. In a further alternative the physical check may be performed by a user, based on instructions presented on the medical device or the user interface.

Figure 5:
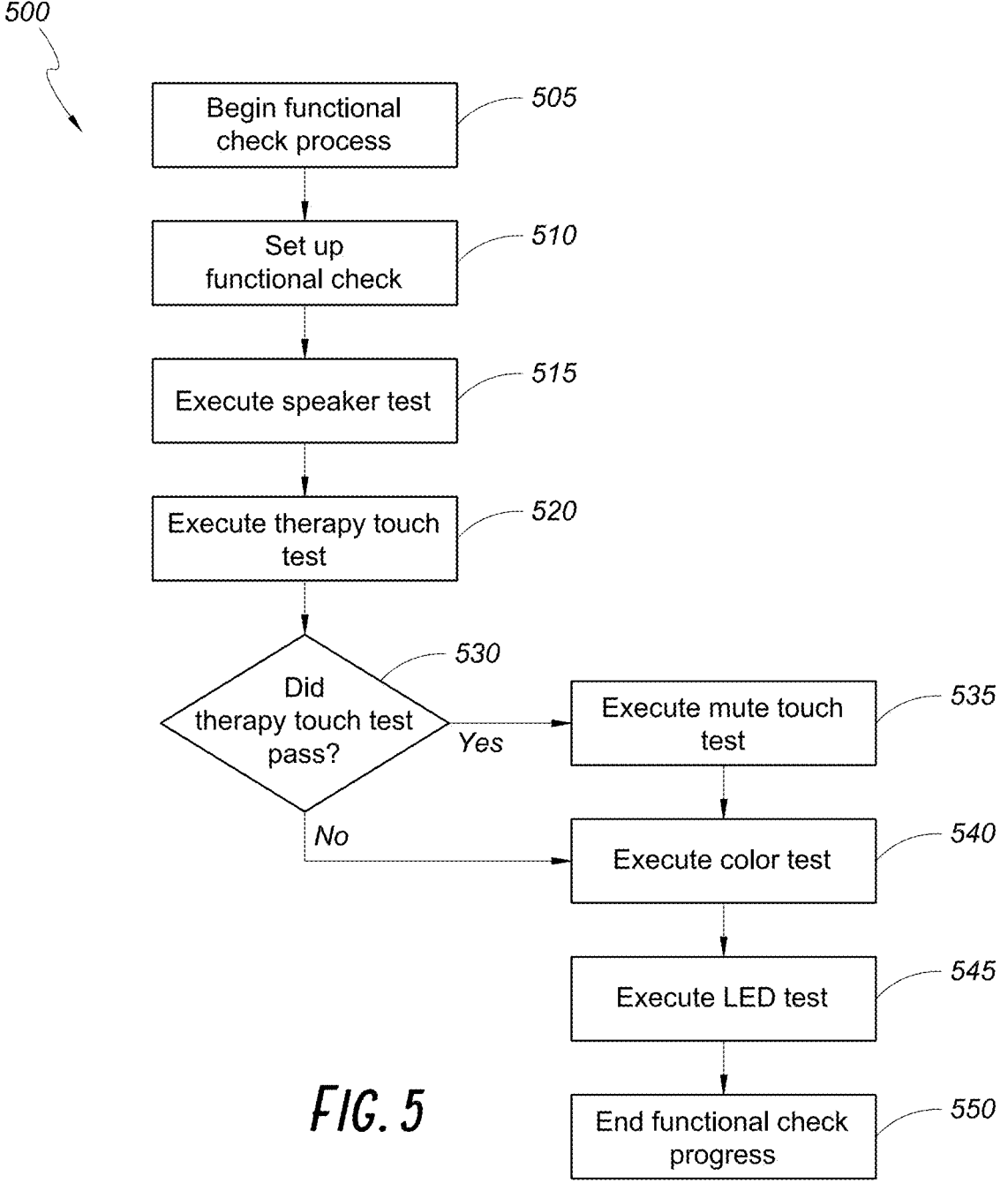
FIG. 5 shows an example flowchart of a method for performing a functional check of a medical device.

FIG. 5 is a process flow diagram of a process 500 for executing a functional check of the medical device 105, 205 according to an embodiment of the present disclosure. The process 500 begins at block 505. At block 510, set up of the functional check is performed. In some embodiments, the functional check is configured to be performed in an automated or semi-automated manner by the maintenance system 100, 200. In particular, the functional check may be configured to be performed in an automated or semi-automated manner by one or more of the processors 115, 215, 120, 220, 222. Accordingly, connection between one or more of the user device 110, 210 and the server 212 with the medical device 105, 205 is established. For example, the user interface 125, 225, 130, 230, 232 may provide images, animations, video presentations, audio presentations, text, combinations thereof, and the like to present instructional guidance to the user on how to set up the maintenance system 100, 200 to prepare for execution of the functional check according to process 500.

In some embodiments, the maintenance system 100, 200 can detect if the medical device 105, 205 is configured properly for execution of the functional check. Illustratively, by way of non-limiting example, the medical device 105, 205 is configured such that a humidification chamber is operational, and both an inspiratory limb and an expiratory limb are connected to the medical device 105, 205. In some embodiments, the medical device 105, 205 is configured to operate in a therapeutic mode so as to enable the process 500 to check the functionality of the medical device 105, 205. The user device 110, 210 may be connected to the medical device 105, 205 by, for example, a USB null-modem cable that appears as a serial port on the medical device 105, 205. The processor 120, 220 of the user device 110, 210 may be configured to execute the process 500, which may be embodied in a set of executable instructions. The user interface 130, 230 of the user device 110, 210 may present messages to and receive responses from the user during execution of the functional check.

If the medical device 105, 205 is disconnected from the user device 110, 210 during the performance of the functional check, a message, such as a modal message, may be displayed to the user to reconnect the medical device 105, 205 to the user device 110, 210. In some embodiments, when connection is re-established, the functional check according to process 500 may continue from the point at which the disconnection occurred. In some embodiments, the functional check may start over at block 505. If, after connection of the medical device 105, 205, the process 500 determines that the connected medical device 105, 205 has a serial number different than the serial number corresponding to a previously connected medical device, then the user interface 130, 230 provides a message, such as a modal message, to the user indicating that the serial number of the connected medical device 105, 205 does not match the serial number of the previously connected medical device and inquires whether the user desires to check the "new" medical device 105, 205. In some embodiments, the message may request the user to re-connect the previously connected medical device that had been previously used for the maintenance check. The message may display on the user interface 125, 225, 130, 230, 232 the serial number of the previously connected medical device. If a provided response to the message indicates that the user desires to check the "new" medical device 105, 205, then another message is provided to the user indicating that a new maintenance test will be started from the beginning, at for example, the electrical safety check.

At block 515, the process 500 executes a speaker test. If the user has reattached the inspiratory limb, the user is instructed to disconnect it again. The user interface 130, 230 of the user device 110, 210 asks whether, when the inspiratory limb was disconnected, the user could hear an auditory alarm. In some embodiments, the user interface 130, 230 of the user device 110, 210 provides an example of the alarm that is expected to be generated by the user interface 125, 225, of the medical device 105, 205 for the purpose of comparison. Illustratively, by way of non-limiting example, a "yes or no" prompt may be displayed for the user to provide a response regarding the inquiry. The process 500 records the outcome of the speaker test and advances to block 520.

At block 520, the process 500 executes a therapy touch test of the user interface 125, 225 of the medical device 105, 205. The user interface 130, 230 of the user device 110, 210 provides instructions to the user to change, through a touch feature of the user interface 125, 225 of the medical device 105, 205, the therapy being delivered by the medical device 105, 205. In response to the change in therapy, the process 500 can detect whether the therapy was changed by the medical device 105, 205. If the user is unable to change the therapy via the user interface 125, 225 on the medical device 105, 205 because, for example, the touch feature of the user interface 125, 225 is not operable, the user can provide user input to the user interface 130, 230 of the user device 110, 210 indicating that the user was not able to successfully change the therapy via the touch feature. The process 500 records the outcome of the touch test, and advances to block 530.

At block 530, the process 500 determines whether the therapy touch test passed or failed. If the therapy touch test passes, the process 500 advances to block 535 to execute a mute touch test. If the therapy touch test fails, the process 500 advances to block 540 to execute a color test.

At block 535, the process 500 executes a second touch test to determine whether a mute button on the user interface 125, 225 of the medical device 105, 205 is operable. If the user has reattached the inspiratory limb to the medical device 105, 205, the user is instructed to disconnect it again to generate a disconnection alarm, including an auditory signal, to be presented on the user interface 125, 225 of the medical device 105, 205. The user interface 130, 230 of the user device 110, 210 instructs the user to press a mute button on the user interface 125, 225 of the medical device 105, 205. The user interface 130, 230 of the user device 110, 210 then inquires whether the alarm sound was muted in response to the user pressing the mute button. Illustratively, by way of non-limiting example, a "yes or no" prompt may be displayed for the user to provide a response regarding the inquiry. The process 500 records the outcome of the touch test, and advances to block 540.

At block 540, the process 500 executes a color test of the user interface 125, 225 of the medical device 105, 205. The user interface 130, 230 of the user device 110, 210 provides instructions to the user to disconnect an inspiratory limb from the medical device 105, 205 to generate a disconnection alarm to be presented on the user interface 125, 225 of the medical device 105, 205. The user is then asked to compare the color of an alarm banner displayed on the user interface 115, 215 of the medical device 105, 205 with a color display presented on the user interface 130, 230 of the user device 110, 210. Illustratively, by way of non-limiting example, a "yes or no" prompt may be displayed for the user to provide a response regarding the comparison of the colors. The process 500 records the outcome of the color test, and advances to block 545.

At block 545, the process 500 executes a check to determine whether a light-emitting diode (LED) properly illuminates. The process 500, executing on the user device 110, 210, causes the LED to illuminate on the user interface 125, 225 of the medical device 105, 205. In some embodiments, the user interface 130, 230 of the user device 110, 210 provides an image of the appearance of the illuminated LED for the purpose of comparison. The user interface 130, 230 of the user device 110, 210 then inquires whether the LED appears on the user interface 125, 225 of the medical device 105, 205. Illustratively, by way of non-limiting example, a "yes or no" prompt may be displayed for the user to provide a response regarding the inquiry. The process 500 records the outcome of the LED test and advances to block 550 where the functional check process 500 ends.

Performance of the functional check is not limited to the order and number of steps described in the process 500. While the functional check according to the process 500 describes the execution of a series of steps in a particular sequence, the individual steps may be performed in any order, unless otherwise specified. Additionally, performance of the functional check does not require execution of all the steps described in the process 500. In some embodiments, the functional check may include additional steps not described in the process 500. In some embodiments, the functional check may not include all steps described in the process 500. One or more steps of the process 500 may be executed by any one of or any combination of the processors 115, 215, 120, 220, 222 or other processors residing in the same devices or other devices.

In some embodiments, the maintenance system 100, 200 may include a performance check. A performance check may include validation that one or more performance characteristics of the medical device 105, 205 are within acceptable limits. A performance characteristic of the medical device 105, 205 may include a piece of information that is available to the processor 115, 215, 120, 220, 222 or a combination of different pieces of information that are available to the processor 115, 215, 120, 220, 222. A performance characteristic of the medical device 105, 205 may comprise, for example but without limitation: a flow rate, a temperature, an electrical resistance or voltage or current, a pressure, or a dew point. In some embodiments, a performance check may include an act wherein the processor 115, 215, 120, 220, 222 measures a performance characteristic of the medical device 105, 205. A performance check may include an act wherein the processor 115, 215, 120, 220, 222 stores the performance characteristic in a storage device associated with one or more of the medical device 105, 205, the user device 110, 210, or the server 212. A performance check may include an act wherein the processor 115, 215, 120, 220, 222 determines whether the medical device 105, 205 has passed the performance check by comparing a performance characteristic to one or more predetermined limit values. A performance check may include an act wherein the processor 115, 215, 120, 220, 222 retrieves one or more predetermined limit values from one of the medical device 105, 205, the user device 110, 210, or the server 212. A performance check may include an act wherein the processor 115, 215, 120, 220, 222 displays a message on the user interface 125, 225, 130, 230, 232 indicating whether the medical device 105, 205 passed or failed the performance check.

If performance of the performance check is interrupted, a message, such as a modal message, may be displayed to the user indicating an interruption has occurred. In some embodiments, if the performance check is re-established, the performance check may continue from the point at which the interruption occurred. In some embodiments, the physical check may start over.

The performance check may include a warmup test. In some embodiments, the warmup test may include a test of the response of a heating element to ensure that the heating element is capable of heating liquid contained in a liquid reservoir to a desired temperature in a desired amount of time. In some embodiments, the desired temperature may be between 30 and 70 degrees Celsius. In some embodiments, the desired temperature may exceed 70 degrees Celsius. In some embodiments, the desired temperature may be less than 30 degrees Celsius. In some embodiments, the desired time may be between 10 and 40 minutes. In some embodiments, the desired time may exceed 40 minutes. In some embodiments, the desired time may be less than 10 minutes.

In some embodiments, a functional check may include validation of correct and safe operation of one or more functional components of the medical device 105, 205, including but not limited to a system health protection component. A functional check of a system health protection component—or a system health protection check—may be difficult to perform as the system health protection component may be contained within the medical device 105, 205 and hence not directly accessible. A system health protection check may include generating an unexpected condition, for example, by providing the system health protection component with a signal that the system health protection component would be expected to detect as unexpected. A system health protection check may be difficult to perform as, in some cases, it may damage the medical device 105, 205.

In some embodiments, a system health protection check may include an act wherein the processor 115, 215, 120, 220, 222 determines whether one or more entry conditions for the system health protection check are satisfied before proceeding with the system health protection check. A system health protection check may include an act wherein the processor 115, 215, 120, 220, 222 displays a message on the user interface 125, 225, 130, 230, 232 informing a user of the status of the one or more entry conditions. In some embodiments, a system health protection check may include an act wherein the processor 115, 215, 120, 220, 222 generates or simulates an unexpected condition and determines a response of the system health protection component to the unexpected condition. In some embodiments, a system health protection check may include an act wherein the processor 115, 215, 120, 220, 222 generates or simulates normal operating conditions and determines a response of the system health protection component during normal operation. A system health protection check may include an act wherein the processor 115, 215, 120, 220, 222 measures an electrical value such as a voltage or logic value in the system health protection component to determine a response of the system health protection component to the unexpected condition. A system health protection check may include an act wherein the processor 115, 215, 120, 220, 222 compares the elapsed time between the generation of an unexpected condition and the triggering of the system health protection component to a predetermined threshold. A system health protection check may include an act wherein the processor 115, 215, 120, 220, 222 displays a result of the functional check on the user interface 125, 225, 130, 230, 232. The result could indicate, for example but without limitation, that the system health protection component does not successfully recognize an unexpected condition, incorrectly identifies an unexpected condition, or is too slow to recognize an unexpected condition. In some embodiments, a system health protection check may include an act wherein the processor 115, 215, 120, 220, 222 displays details of a specific unexpected condition and/or a suggested course of action to address the unexpected condition.

In some embodiments, the medical device 105, 205 may include hardware and/or software capable of generating an unexpected condition. The medical device 105, 205 may include an electrical circuit or component used to simulate or generate an unexpected condition. Such an electrical circuit or component may be beneficial in that it may be used to test both a hardware response and a software response of a system health protection component of the medical device 105, 205 to an unexpected condition. Software of the medical device 105, 205 may also be used to generate or simulate an unexpected condition. An unexpected condition simulated in software may be used to test the response of a system health protection component of the medical device 105, 205 to an unexpected condition. The hardware response of a system health protection component of the medical device 105, 205 may need to be tested separately to that of the software response.

An example of a system health protection component is a transient current detector (TCD), similar to that disclosed in U.S. Pat. No. 6,598,604, which is herein incorporated by reference in its entirety. In some embodiments, the medical device 105, 205 may include a TCD that may detect a transient current or an overcurrent in an electrical component, including but not limited to a heating element of the medical device 105, 205. A TCD may detect a transient current by monitoring current through the heating element of the medical device 105, 205 and activating a current interrupter if there is a rapid change in current that exceeds a predetermined change threshold. A TCD may detect an overcurrent by monitoring current through the heating element and by activating a current interrupter if the current exceeds a predetermined current threshold. The TCD is a fault protection circuit for a respiratory conduit heater element in a respiratory humidification system. The TCD is used as a fault protection circuit with a heater wire in an inspiratory limb 3. The circuit includes a spark detector and an overcurrent detector. The spark detector may include a two winding transformer, a center tapped two winding transformer and/or a high pass filtered inductor. The TCD further includes a semiconductor switching configuration. Once the protection circuit detects a change in current over a certain level, or the average level raises above a threshold, then the current in the heater element is interrupted for a preset period.

A functional check of a TCD may include an act wherein the processor 115, 215, 120, 220, 222 causes a transient, or rapid change in current, to be generated that exceeds a change threshold for a heating element of the medical device 105, 205. A functional check of a TCD may include an act wherein the processor 115, 215, 120, 220, 222 causes an overcurrent to be generated that exceeds a current threshold for a heating element of the medical device 105, 205. A transient or overcurrent may be generated by the medical device 105, 205, the user device 110, 210, or by some other external device, for example a signal generator. The medical device 105, 205 or the user device 110, 210 may include electrical circuitry or software to generate or simulate an unexpected condition, including but not limited to an inbuilt signal generator. A functional check of a TCD may include an act wherein the processor 115, 215, 120, 220, 222 determines whether the current interrupter has been triggered, and thus whether an unexpected condition has been recognized.

Figure 6:
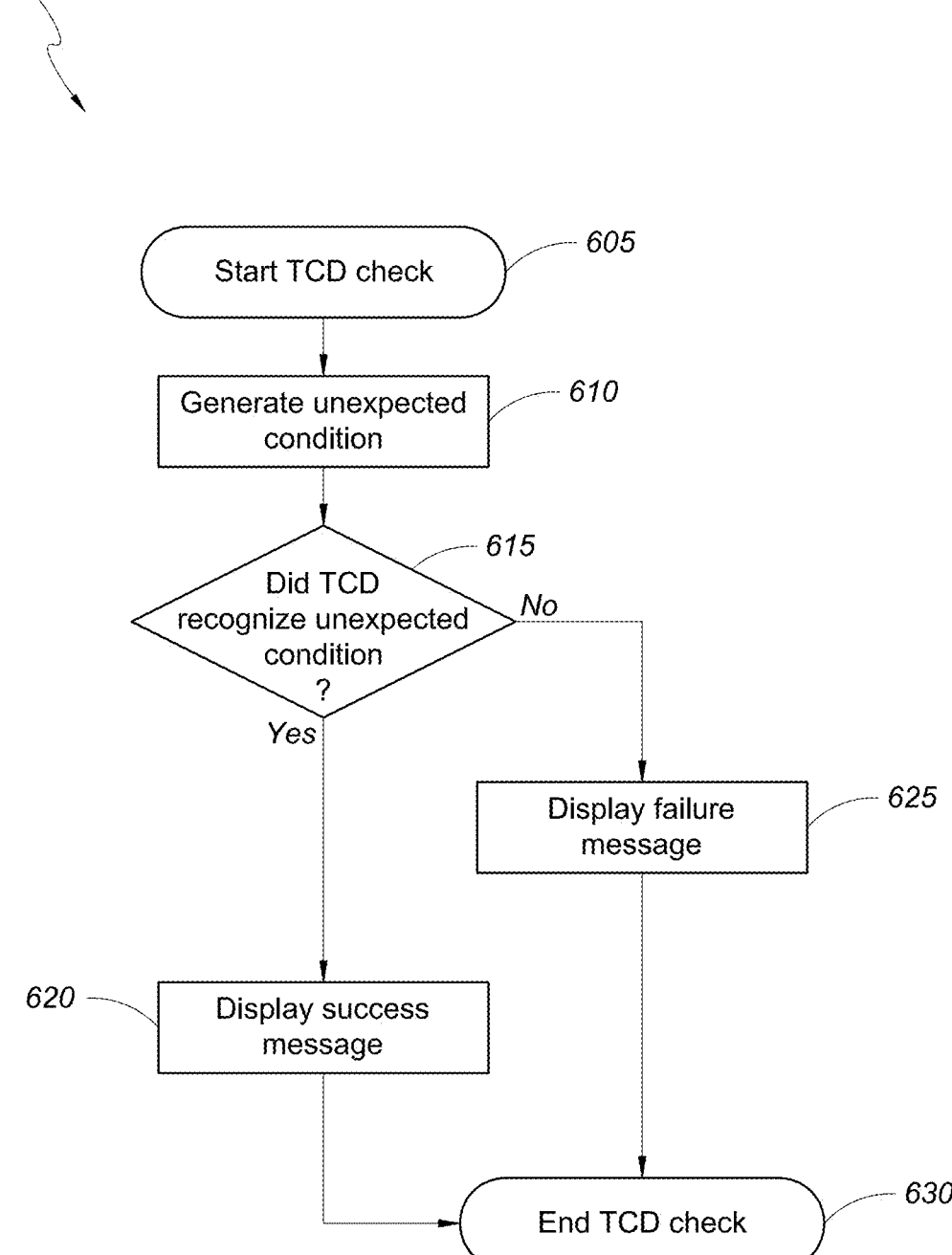
FIG. 6 shows an example flowchart of a method for performing a functional check of a transient current detector (TCD) of a medical device.

FIG. 6 shows an example flowchart of a method 600 for performing a functional check of a TCD of the medical device 105, 205. The method 600 starts at block 605.

At block 605, the processor 115, 215, 120, 220, 222 initiates the functional check of the TCD. In an alternate embodiment, the functional check of the TCD may be initiated by interaction of a user with the user interface 125, 225, 130, 230, 232. The method 600 then proceeds to block 610.

At block 610, the processor 115, 215, 120, 220, 222 generates an unexpected condition by causing a transient current or overcurrent to be generated or simulated. The method 600 then proceeds to block 615.

At block 615, the processor 115, 215, 120, 220, 222 determines a response of the TCD to the unexpected condition (for example, the transient or overcurrent condition); if the response of the TCD was correct (for example, activating a current interrupter in response to the unexpected condition), the method 600 proceeds to block 620, otherwise the method 600 proceeds to block 625.

At block 620, the processor 115, 215, 120, 220, 222 displays a message on the user interface 125, 225, 130, 230, 232 indicating that the functional check of the TCD succeeded. The method 600 then ends.

At block 625, the processor 115, 215, 120, 220, 222 displays a message on the user interface 125, 225, 130, 230, 232 indicating that the functional check of the TCD failed. The method 600 then proceeds to block 630.

At block 630, the processor 115, 215, 120, 220, 222 concludes the functional check of the TCD. The method 600 then ends.

If performance of the functional check of the TCD according to process 600 is interrupted, a message, such as a modal message, may be displayed to the user indicating an interruption has occurred. In some embodiments, if the functional check of the TCD is re-established, the functional check of the TCD may continue from the point at which the interruption occurred. In some embodiments, the functional check of the TCD may start over at block 605.

Performance of the functional check of the TCD is not limited to the order and number of steps described in the process 600. While the functional check of the TCD according to the process 600 describes the execution of a series of steps in a particular sequence, the individual steps may be performed in any order, unless otherwise specified. Additionally, performance of the functional check of the TCD does not require execution of all the steps described in the process 600. In some embodiments, the functional check of the TCD may include additional steps not described in the process 600. In some embodiments, the functional check of the TCD may not include all steps described in the process 600. One or more steps of the process 600 may be executed by any one of or any combination of the processors 115, 215, 120, 220, 222 or other processors residing in the same devices or other devices.

The medical device 105, 205 may include a heating element. The heating element may include a heater plate or a heater wire and may be configured to heat gases within the medical device 105, 205. The medical device 105, 205 may include a thermal cutout device configured to cut power to the heating element when a temperature reaches or exceeds a predetermined threshold. A functional check may include an act wherein the processor 115, 215, 120, 220, 222 validates the correct operation of the thermal cutout device of the medical device 105, 205.

Figure 7:
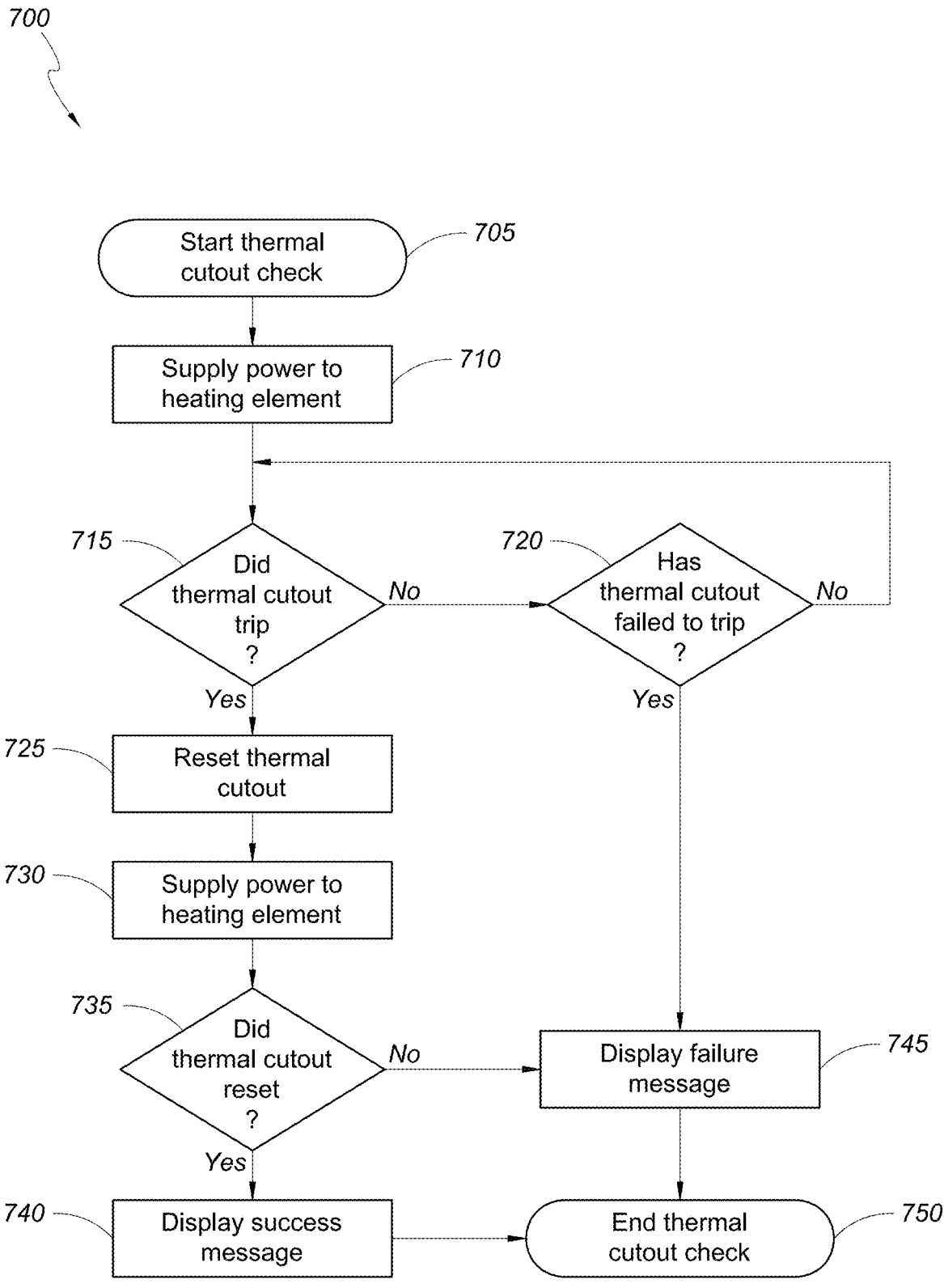
FIG. 7 shows an example flowchart of a method for performing a functional check of a thermal cutout of a medical device.

FIG. 7 shows an example flowchart of a method 700 for performing a functional check of a thermal cutout device of the medical device 105, 205. The method 700 starts at block 705.

At block 705, the processor 115, 215, 120, 220, 222 initiates the functional check of the thermal cutout device. In an alternate embodiment, the functional check of the thermal cutout device may be initiated by interaction of a user with the user interface 125, 225, 130, 230, 232. The method 700 then proceeds to block 710.

The heating element may include a heater plate configured to heat and/or vaporize liquid in a humidification chamber adjacent to the heater plate. In some such embodiments, the processor 115, 215, 120, 220, 222 may display a message on the user interface 125, 225, 130, 230, 232 instructing a user to ensure there is no liquid in the humidification chamber to avoid damping or slowing the rise time of the heater plate temperature.

At block 710, the processor 115, 215, 120, 220, 222 causes power to be supplied to the heating element. In an embodiment, the processor 115, 215, 120, 220, 222 may cause full power (for example, 100% duty cycle) to be supplied to the heating element. In an embodiment, the processor 115, 215, 120, 220, 222 may start a timer. The method 700 then proceeds to block 715.

At block 715, the processor 115, 215, 120, 220, 222 determines a response of the thermal cutout device to the rising temperature of the heating element. In an embodiment, the processor 115, 215, 120, 220, 222 may determine that the thermal cutout device has tripped by measuring power supplied to the heating element, as after the thermal cutout device has tripped, the power supplied to the heating element will drop. In an embodiment, the processor 115, 215, 120, 220, 222 may determine that the thermal cutout device has tripped by measuring a temperature, as after the thermal cutout device has tripped, a relevant temperature will drop. If the thermal cutout device has not tripped, the method 700 proceeds to block 720, otherwise the method 700 proceeds to block 725.

At block 720, the processor 115, 215, 120, 220, 222 determines whether the thermal cutout device has failed the functional check by not tripping. In an embodiment, the processor 115, 215, 120, 220, 222 may determine whether the thermal cutout device has failed the functional check by comparing the value of the timer to a predetermined maximum time value. If the value of the timer has reached or exceeded the predetermined maximum time value, then the thermal cutout device has failed the functional check. In an embodiment, the predetermined maximum time value is between 4 and 6 minutes. In an embodiment, the predetermined maximum time value is about 5 minutes. In an embodiment, the processor 115, 215, 120, 220, 222 may determine whether the thermal cutout device has failed the functional check by comparing the value of the measured temperature to a predetermined maximum temperature value. If the value of the measured temperature has reached or exceeded the predetermined maximum temperature value, then the thermal cutout device has failed the functional check. In an embodiment, the predetermined maximum temperature value is 160 degrees Celsius. In an embodiment, the processor 115, 215, 120, 220, 222 may determine whether the thermal cutout device has failed the functional check by displaying a message on the user interface 125, 225, 130, 230, 232 instructing a user to confirm a status of the thermal cutout device and to input that status. If the thermal cutout device has failed the functional check, the method 700 proceeds to block 745, otherwise the method 700 returns to block 715. If the thermal cutout device has not failed the functional check, the method 700 may wait for a predetermined period of time before returning to block 715.

At block 725, the processor 115, 215, 120, 220, 222 causes a message to be displayed on the user interface 125, 225, 130, 230, 232 instructing a user to manually reset the thermal cutout device and then to confirm that the thermal cutout device has been reset. In an embodiment, the processor 115, 215, 120, 220, 222 may automatically reset the thermal cutout device. The method 700 then proceeds to block 730.

At block 730, the processor 115, 215, 120, 220, 222 causes power to be supplied to the heating element. The method 700 then proceeds to block 735.

At block 735, the processor 115, 215, 120, 220, 222 determines whether the thermal cutout device has reset properly. In an embodiment, the processor 115, 215, 120, 220, 222 determines whether the thermal cutout device has reset properly by measuring power supplied to the heating element, as after the thermal cutout device has reset properly, the power supplied to the heating element will rise. In an embodiment, the processor 115, 215, 120, 220, 222 determines whether the thermal cutout device has reset properly by measuring a temperature, as after the thermal cutout device has reset properly, a relevant temperature will rise. If the thermal cutout device has reset properly, the method 700 proceeds to block 740, otherwise, the method 700 proceeds to block 745.

At block 740, the processor 115, 215, 120, 220, 222 displays a message on the user interface 125, 225, 130, 230, 232 indicating that the functional check of the thermal cutout device succeeded. The method 700 then proceeds to block 750.

At block 745, the processor 115, 215, 120, 220, 222 displays a message on the user interface 125, 225, 130, 230, 232 indicating that the functional check of the thermal cutout device failed. The method 700 then proceeds to block 750.

At block 750, the processor 115, 215, 120, 220, 222 concludes the functional check of the thermal cutout device. The method 700 then ends.

If performance of the functional check of the thermal cutout device according to process 700 is interrupted, a message, such as a modal message, may be displayed to the user indicating an interruption has occurred. In some embodiments, if the functional check of the thermal cutout device is re-established, the functional check of the thermal cutout device may continue from the point at which the interruption occurred. In some embodiments, the functional check of the thermal cutout device may start over at block 705.

Performance of the functional check of the thermal cutout device is not limited to the order and number of steps described in the process 700. While the functional check of the thermal cutout device according to the process 700 describes the execution of a series of steps in a particular sequence, the individual steps may be performed in any order, unless otherwise specified. Additionally, performance of the functional check of the thermal cutout device does not require execution of all the steps described in the process

700. In some embodiments, the functional check of the thermal cutout device may include additional steps not described in the process 700. In some embodiments, the functional check of the thermal cutout device may not include all steps described in the process 700. One or more steps of the process 700 may be executed by any one of or any combination of the processors 115, 215, 120, 220, 222 or other processors residing in the same devices or other devices.

In some embodiments, a functional check may include an act wherein the processor 115, 215, 120, 220, 222 validates the correct operation of a software module or process of the medical device 105, 205. For example, but without limitation, the processor 115, 215, 120, 220, 222 may validate that a boot loader executes correctly or that a watchdog or other monitoring process is able to reset the medical device 105, 205.

In some embodiments, a functional check may include an act wherein the processor 115, 215, 120, 220, 222 validates the correct operation of an electrical component of the medical device 105, 205. For example, but without limitation, the processor 115, 215, 120, 220, 222 may validate that a relay correctly operates to control power supplied to a heating element; a sensor correctly measures, for example, a temperature, pressure, humidity, or flow rate; or an analog to digital converter correctly converts an analog signal to a digital signal.

In some embodiments, a functional check may include an act wherein the processor 115, 215, 120, 220, 222 validates the correct operation of a mechanical component of the medical device 105, 205. A functional check of a mechanical component of the medical device 105, 205—or a mechanical component check—may include an act wherein the processor 115, 215, 120, 220, 222 activates a function of, or related to, the mechanical component. In some embodiments, a mechanical component check may include an act wherein the processor 115, 215, 120, 220, 222 displays a message on the user interface 125, 225, 130, 230, 232 instructing a user to activate a function of, or related to, the mechanical component. In some embodiments, a mechanical component check may include an act wherein the processor 115, 215, 120, 220, 222 displays a message on the user interface 125, 225, 130, 230, 232 instructing a user to confirm correct functioning of the mechanical component. For example but without limitation, a mechanical component check may include an act wherein the processor 115, 215, 120, 220, 222 instructs a user to validate a discrimination of the user's touch on a touch screen, the actuation of a button, or the correct operation of a speaker or a light emitting diode (LED).

As a particular example, a mechanical component check may include an act wherein the processor 115, 215, 120, 220, 222 causes test data, such as but not limited to a word or an image, to be displayed on the user interface 125, 225 of the medical device 105, 205, and then displays a message on the user interface 125, 225, 130, 230, 232 instructing a user to confirm that the test data is correctly displayed on the user interface 125, 225 of the medical device 105, 205. The processor 115, 215, 120, 220, 222 may cause the test data to be duplicated on the user interface 130, 230, 232 of the user device 110, 210 or the server 212, so that a user can make a visual comparison. Such a mechanical component check of the user interface 125, 225 of the medical device 105, 205 may be used to validate functionality, such as the proper display of color.

In some embodiments, the processor 115, 215, 120, 220, 222 executes a mechanical component check that validates the correct operation of a speaker of the medical device 105, 205. The processor 115, 215, 120, 220, 222 may cause a sound or tone to be generated using the speaker of the medical device 105, 205. The processor 115, 215, 120, 220, 222 may determine whether the mechanical component check of the speaker succeeded or failed by displaying a message on the user interface 125, 225, 130, 230, 232 instructing a user to confirm that the sound or tone was generated, was not distorted, and/or was of sufficient loudness. For example, the processor 115, 215, 120, 220, 222 may cause an audible alarm of the medical device 105, 205 to be activated. In some embodiments, the processor 115, 215, 120, 220, 222 may determine whether the mechanical component check of the speaker succeeded or failed by using a microphone of the medical device 105, 205 or the user device 110, 210 to record the generated sound or tone. The processor 115, 215, 120, 220, 222 may display a message on the user interface 125, 225, 130, 230, 232 indicating whether the mechanical component check of the speaker succeeded or failed.

In some embodiments, the processor 115, 215, 120, 220, 222 executes a mechanical component check that validates the correct operation of the touch screen functionality of the user interface 125, 225 of the medical device 105, 205. The processor 115, 215, 120, 220, 222 may cause an image or icon to be displayed on the user interface 125, 225 of the medical device 105, 205. The processor 115, 215, 120, 220, 222 may display a message on the user interface 125, 225, 130, 230, 232 instructing a user to press the image or icon displayed on the user interface 125, 225 of the medical device 105, 205. For example, the processor 115, 215, 120, 220, 222 may cause an audible alarm of the medical device 105, 205 to be activated and cause an icon representing a mute button to be displayed on the user interface 125, 225 of the medical device 105, 205 for a user to press to mute the audible alarm. The processor 115, 215, 120, 220, 222 may determine whether the mechanical component check of the touch screen functionality succeeded or failed by confirming whether the touch functionality of the user interface 125, 225 recognized the user's touch. The processor 115, 215, 120, 220, 222 may display a message on the user interface 125, 225, 130, 230, 232 indicating whether the mechanical component check of the touch screen functionality succeeded or failed.

In some embodiments, the processor 115, 215, 120, 220, 222 executes a mechanical component check that validates the correct operation of a button of the user interface 125, 225 of the medical device 105, 205. The processor 115, 215, 120, 220, 222 may display a message on the user interface 125, 225, 130, 230, 232 instructing a user to press a button of the user interface 125, 225 of the medical device 105, 205. For example, the message may instruct a user to hold down a power button of the medical device 105, 205 to initiate a restart. In some embodiments, the processor 115, 215, 120, 220, 222 may determine whether the mechanical component check of the button succeeded or failed by confirming whether the button actuated, for example, by completing an electrical circuit. The processor 115, 215, 120, 220, 222 may display a message on the user interface 125, 225, 130, 230, 232 indicating whether the mechanical component check of the button succeeded or failed.

In some embodiments, the processor 115, 215, 120, 220, 222 executes a mechanical component check that validates the correct display of color on the user interface 125, 225 of the medical device 105, 205. The processor 115, 215, 120, 220, 222 may cause an area—for example but not limited to a square, a circle, or another bounded region—to be displayed in a selected color or pattern of colors on the user interface 125, 225 of the medical device 105, 205. The processor 115, 215, 120, 220, 222 may display a message on the user interface 125, 225, 130, 230, 232 instructing a user to confirm that the correct color or pattern of colors is displayed on the user interface 125, 225 of the medical device 105, 205. The processor 115, 215, 120, 220, 222 may display the selected color or pattern of colors on the user interface 130, 230, 232 of the user device 110, 210 or the server 212 so the user can make a visual comparison. For example, the processor 115, 215, 120, 220, 222 may cause a selected screen or webpage to be displayed on the user interface 125, 225 of the medical device 105, 205 and duplicate the screen or webpage on the user interface 130, 230, 232 of the user device 110, 210 or the server 212 for comparison. The processor 115, 215, 120, 220, 222 may display a message on the user interface 125, 225, 130, 230, 232 indicating whether the mechanical component check of the display of colors succeeded or failed. In some embodiments, the processor 115, 215, 120, 220, 222 may execute similar mechanical component checks of the display of colors using multiple colors, simultaneously or in sequence, or an image or a test pattern, for example but without limitation.

In some embodiments, the processor 115, 215, 120, 220, 222 executes a mechanical component check that validates the correct operation of a light-emitting diode (LED) of the medical device 105, 205. The processor 115, 215, 120, 220, 222 may activate an LED of the medical device 105, 205, continuously or in a pulsed pattern, for a predetermined period of time. In some embodiments, the processor 115, 215, 120, 220, 222 may determine whether the mechanical component check of the LED succeeded or failed by displaying a message on the user interface 125, 225, 130, 230, 232 instructing a user to confirm that the LED was activated properly. In some embodiments, the processor 115, 215, 120, 220, 222 may determine whether the mechanical component check of the LED succeeded or failed by using a camera of the medical device 105, 205 or the user device 110, 210 to record the displayed LED. The processor 115, 215, 120, 220, 222 may display a message on the user interface 125, 225, 130, 230, 232 indicating whether the mechanical component check of the LED succeeded or failed. In some embodiments, the processor 115, 215, 120, 220, 222 may execute similar mechanical component checks of multiple LEDs, simultaneously, in sequence, or in another predetermined pattern. The processor 115, 215, 120, 220, 222 may display information on the user interface 125, 225, 130, 230, 232 indicating the location(s) and/or sequence of activation of the LED(s).

In some embodiments, a functional check may include an act wherein the processor 115, 215, 120, 220, 222 validates the correct operation of a component configured to couple with the medical device 105, 205. In some embodiments, a coupleable component may have a limited duration or lifetime of use. In some embodiments, a coupleable component may be reusable. A coupleable component may include a storage device, for example but without limitation an electrically erasable programmable read-only memory (EEPROM). As an example for the respiratory humidifier 5, a coupleable component includes the sensor cartridge 6.

A functional check of a coupleable component may include an act wherein the processor 115, 215, 120, 220, 222 retrieves status data from such a storage device of the coupleable component, wherein the status data may comprise, for example but without limitation, usage or lifetime information such as the date and/or time the coupleable component was first used with the medical device 105, 205; the total amount of time—either elapsed time or time-in-use—the coupleable component has been used with the medical device 105, 205; the date of manufacture of the coupleable component, or any other information related to the status of the coupleable component. The processor 115, 215, 120, 220, 222 may retrieve information from the medical device 105, 205, the user device 110, 210, the server 212, or the coupleable component relating to a recommended lifetime or usage information for the coupleable component. The processor 115, 215, 120, 220, 222 may determine a result of the functional check of the coupleable component by comparing the status data retrieved from the coupleable component against the recommended lifetime or usage information. The processor 115, 215, 120, 220, 222 may display a message on the user interface 125, 225, 130, 230, 232 that provides the result to a user. The message may include information relating to the remaining lifetime of the coupleable component. For example, the message may indicate that the coupleable component should be replaced when the coupleable component's usage or lifetime is within a certain percentage of the recommended usage or lifetime, or when the coupleable component's usage or lifetime is projected to reach a certain percentage of the recommended usage or lifetime before a next scheduled service. The coupleable component can be a sensor cartridge 6 that is removably coupleable to a respiratory humidifier 5 (i.e. a medical device).

If performance of a functional check is interrupted, a message, such as a modal message, may be displayed to the user indicating an interruption has occurred. In some embodiments, if the functional check is re-established, the functional check may continue from the point at which the interruption occurred. In some embodiments, the functional check may start over.

In some embodiments, the processor 115, 215, 120, 220, 222 may determine that one or more software modules of the medical device 105, 205 should be updated or upgraded. The processor 115, 215, 120, 220, 222 may retrieve a software upgrade or update from a storage device associated with one of the user device 110, 210 or the server 212. The processor 115, 215, 120, 220, 222 may initiate an upgrade or update of the software of the medical device 105, 205 using the retrieved software upgrade or update.

In some embodiments, the maintenance system 100, 200 executes one or more self-tests. In some embodiments, the maintenance system 100, 200 executes one or more self-tests regardless of each particular self-test's outcome. Some self-tests may require user interaction. Illustratively, by way of non-limiting example, checks of the user interface 125, 225 of the medical device 105, 205 may require the user to observe visual, tactile, auditory, or other forms of communication provided by the user interface 125, 225 and to provide an assessment in response to the observed communications. Another non-limiting example of a self-test that may require user interaction includes a heater plate thermal cutout test that applies full power to the heater plate until the heater plate reaches a predetermined temperature (such as, for example, 160° C.) that exceeds the temperature at which the thermal cutout device is configured to cut power. The self-test is able to automatically determine if the thermal cutout device operated correctly to cut power delivery to the heater plate before the heater plate reached the predetermined temperature. A user may be needed to reset the thermal cutout device after the test has been completed.

Some of the self-tests may execute autonomously and may be implemented by, for example, software instructions executing on the processor 115, 215, 120, 220, 222. Illustratively, by way of non-limiting example, autonomous self-tests may include a transient current test including setting a heater wire duty cycle to a level that is more likely than other levels to trip the transient current detector (TCD), such as, for example, 50%; activating the heating wire; applying a pulse to the TCD test circuit during an AC peak, determining whether the TCD is triggered, and checking the TCD activation period.

A heater switch test (which may be used for either or both the heater plate and the heater wire circuits) may be executed autonomously, including (1) turning off a safety relay, turning on a heater switch, and determining whether the current and voltage of the heater are at zero; (2) turning on the safety relay, turning off the heater switch, and determining whether the current and voltage of the heater are at zero; and (3) turning on the safety relay, turning on the heater switch, and determining whether the current and voltage of the heater are at zero.

An infant relay self-test may be executed autonomously. An infant relay circuit is a safety feature that does not allow two heater wires to be activated concurrently. The self-test includes enabling an infant relay, activating a first heater wire, and determining whether there is voltage on a second heating wire, and attempting to activate the first and second heating wires concurrently.

A heater plate thermistor self-test may be executed autonomously by applying power to the heater plate and determining whether the heating plate reaches a predetermined threshold within a predetermined period of time, for example, 60° C. within five minutes.

A watchdog timer self-test may be autonomously executed by causing a boot loader to not toggle on the watchdog timer during the processor's 115, 215 first initialization ("booting up") and determining whether the watchdog timer correctly resets the processor 115, 215 when it is un-toggled.

A temperature measurement self-test may be autonomously executed by checking if an analog-to-digital converter (ADC) value is within predefined limits and reporting a short/open circuit if the ADC value is beyond the predefined limits; and checking the ADC values of on-board calibration resistors, and reporting an unexpected condition if the checked ADC values are outside of the values of the on-board calibration resistors.

A patient-end sensor overheat self-test may be autonomously executed by trimming back an overheat threshold in and ADC to ensure it is within bounds, activating a self-test trigger to simulate overheat conditions, and determining whether an overheat signal is asserted and power is cut off to a heating wire in response to the simulated overheat condition.

If performance of the self-tests are interrupted, a message, such as a modal message, may be displayed to the user indicating an interruption has occurred. In some embodiments, if the self-tests are re-established, the self-tests may continue from the point at which the interruption occurred. In some embodiments, the self-tests may start over.

Figure 8A:
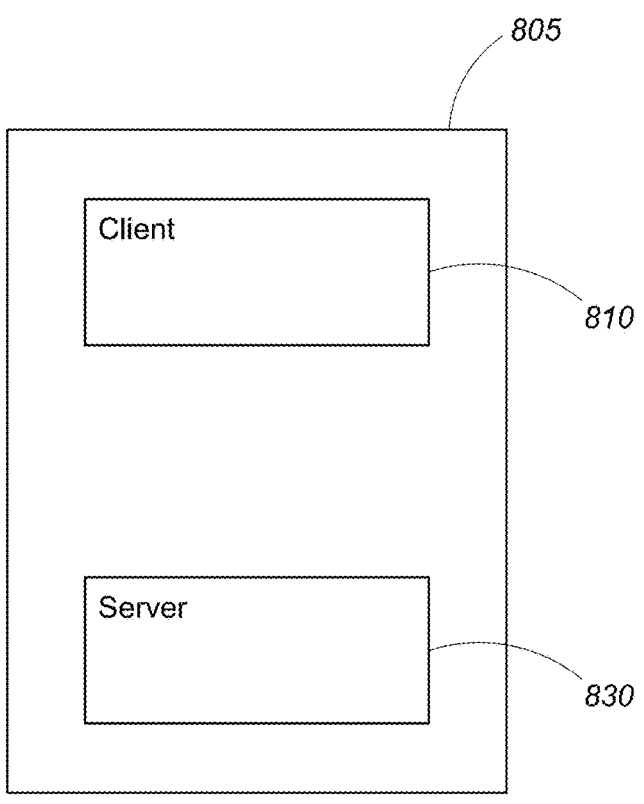
FIG. 8A shows an example block diagram of a maintenance software application.

As illustrated in FIG. 8A, the maintenance system 100, 200 includes a maintenance software application 805 that implements various maintenance checks of the medical device 105, 205 disclosed herein. The maintenance application 805 may automate some or all parts of these tests and provide diagnostic information regarding the state of the medical device 105, 205 to provide a simple work flow for maintenance tasks.

In an embodiment, the maintenance application 805 provides a maintenance check sequence to the user. The sequence is a semi-automated test sequence aimed at ensuring that essential functions and safety features of the medical device 105, 205 are performing as expected. In some embodiments, the user will be referred to a user manual for information on how to service the medical device 105, 205 upon failure of any of the checks in the maintenance check sequence.

In some embodiments, the maintenance application 805 may be implemented as a web application using a client-server architecture, including a client component 810 and a server component 830. In some embodiments, both the client component 810 and the server component 830 may execute on the user device 110, 210 or on the server 212, and an Internet connection between the user device 110, 210 and the server 212 is not required for operation. In some embodiments, the client component 810 and the server component 830 may execute on different computing devices, such as different user devices 210, on different servers 212, or one each on the user device 210 and the server 212, and a network connection (such as a LAN, WAN, cellular, Internet connection, or the like) may be used for communication between the different computing devices.

The client component 810 may be implemented in a web browser environment and is responsible for displaying content on the user interface 125, 225, 130, 230, 232 and for handling user interactions, such as user input. Upon launching the maintenance application 805, a web browser instance associated with the client component 810 pointing to the address of the server component 830 is initiated to display a page on the user interface 125, 130, 232. The web browser instance then requests the web page and any related assets from the server component 830, and the server component 830 either generates the page via a templating engine or serves up static files directly. In some embodiments, pages are presented on the user interface 125, 225, 130, 230, 232 using standard HTML5+CSS3+JavaScript which are compatible with most modern web browsers. In some embodiments, alternative web technologies are used.

Figure 8B:
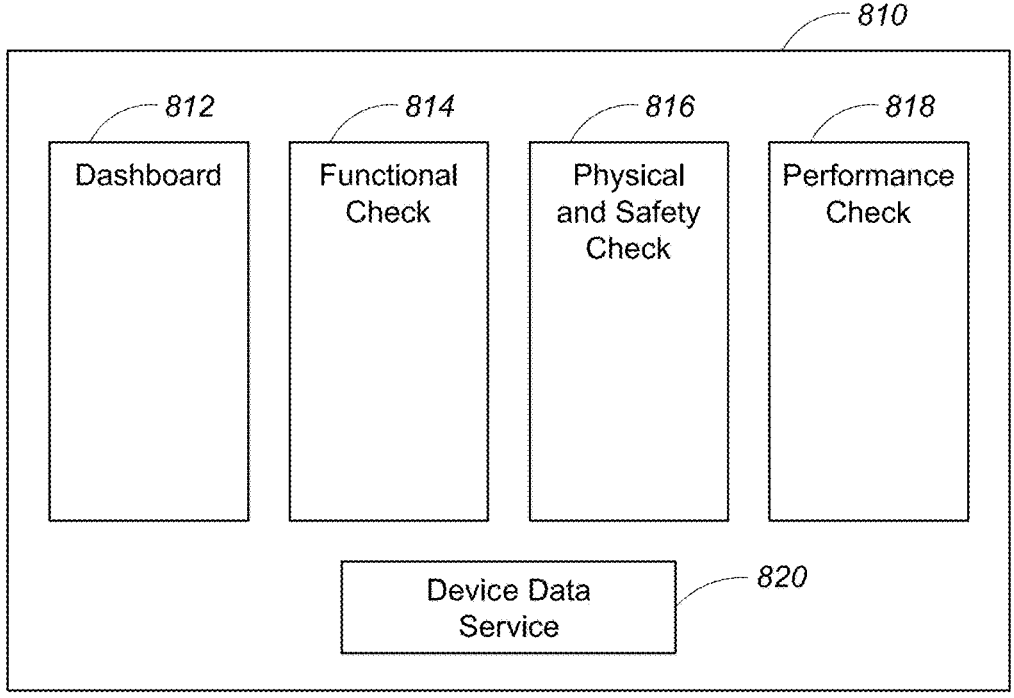
FIG. 8B shows an example block diagram of software modules of a client component.

The client component 810 includes multiple views for the different functionalities in the maintenance application 805. FIG. 8B illustrates software modules of the client component 810 according to an embodiment, including a dashboard module 812, a functional check module 814, a physical and safety check module 816, a performance check module 818, and a device data service module 820.

The dashboard module 812 may present information regarding the medical device 105, 205 including but not limited to identification information such as a device serial number, installed software version information, serial number of a coupleable component, expiry date/time of the coupleable component, due date of the annual maintenance check, date the last annual maintenance check was completed, and device status (for example, connectivity and alarm state). In some embodiments, the information regarding the medical device 105, 205 is aggregated at the server 212, whether owned by the manufacturer of the medical device 105, 205 or the hospital. The aggregated data could be used for asset tracking and other purposes. When the medical device 105, 205 is connected to the maintenance application 805, the dashboard module 812 will be able to read the last date a maintenance check had been performed on the medical device 105, 205 and display when the next maintenance check is due. As an example for the respiratory humidifier 5, the dashboard module 812 may present information including, among other information as previously described, the serial number of the sensor cartridge 6 and the expiry date/time of the sensor cartridge 6, and may read usage information associated with the sensor cartridge 6 and determine the remaining usage life of the sensor cartridge 6 which may be presented in a number of remaining hours or by a fixed date after which the sensor cartridge 6 should be replaced. If the sensor cartridge 6 has expired, the dashboard module 812 will notify the user of this fact and request its replacement via the user interface 9.

The functional check module 814 may enable execution of functional checks of the medical device 105, 205. In some embodiments, the functional check module 814 includes a user interface check wizard to interactively guide the user through the process of checking the user interface 125, 225 of the medical device 105, 205. The functional check module 814 may also include a program to interactively guide the user through the processes of checking a transient current detector in the medical device 105, 205. The functional check module 814 may include a program to present the results of the functional check in the form of a report.

The physical and safety check module 816 may enable execution of physical and safety checks of the medical device 105, 205. In some embodiments, the physical and safety check module 816 includes a safety check wizard to interactively guide the user through the process of checking electrical safety features of the medical device 105, 205. The physical and safety check module 816 may also include a physical check wizard to interactively guide the user through the process of checking various physical properties of the medical device 105, 205. The physical and safety check module 816 may include a program to present the results of the physical and/or safety checks in the form of a report.

The performance check module 818 may enable execution of one or more performance checks of the medical device 105, 205, including without limitation a warm-up check of the medical device 105, 205. In some embodiments, the performance check module 818 includes a performance check wizard to interactively guide the user through the process of checking the performance of the medical device 105, 205 in an operational scenario. The performance check module 818 may present, via the user interface 125, 225, 130, 230, 232, graphical information indicative of the performance checks as the checks are being executed and once the checks have been completed. The performance check module 818 may include a program to present the results of the performance checks in the form of a report.

The device data service module 820 manages communications between the client component 810 and the server component 830 from the client side of the interface.

The server component 830 communicates with the medical device 105, 205 over a communication link, such as by way of non-limiting example, a USB null modem cable. The server component 830 handles such communication and acts as the interface between the medical device 105, 205 and the rest of the maintenance application 805 (such as the client component 810) by gathering device data from the medical device 105, 205 and by issuing commands to the medical device 105, 205 upon the request of the maintenance application 805. In some embodiments, only one medical device 105, 205 is connected to the user device 110, 210 or the server 212 at any given time. In some embodiments, more than one medical device 105, 205 may be connected to the user device 110, 210 or the server 212 at a given time.

In operation, according to some embodiments of the maintenance application 805, a web browser associated with the client component 810 creates a dynamic user interface to avoid the need to refresh pages and for the server component 830 to keep track of client states. A model-view-controller (MVC) paradigm is used to structure the client component 810. The model in this instance is primarily the device data which is requested by the server component 830 from a representational state transfer application program interface via, for example, AJAX and HTTP requests. The view takes this data and formats it for display, while the MVC takes in user inputs and sends the appropriate commands back to the server component 830 in order to manipulate the model.

Establishing Internet access in a hospital environment, where the medical device 105 is frequently used, may be challenging due to, for example, security and confidentiality constraints. Accordingly, in some embodiments, the server component 830 and all of the server-end applications may be installed and run on the user device 110. The user interface 130 is accessed via a web browser pointing to a local address. In some embodiments, the communication to the medical device 105 is achieved via an FTDI USB null-modem cable which appears as a serial port on the user device 110. In some embodiments, the server component 830 interfaces with one medical device 105. In some embodiments, the server component 830 may run multiple instances of communication and application modules on the user device 110 to interface with more than one medical device 105.

Some environments in which the medical device 205 operates may permit access to networks such the Internet. In such circumstances, the maintenance system 200 may be implemented in a distributed manner. For example, in some embodiments, the maintenance application 805 may be installed on the server 212. In some embodiments the server 212 is owned, operated, or otherwise controlled by a manufacturer of the medical device 205. In some embodiments, the server 212 is owned, operated, or otherwise controlled by a hospital. Advantageously, when the maintenance application 805 is hosted centrally on the server 212, the maintenance application 805 may be implemented in an on demand mode as, for example, software as a service (SaaS). Such an implementation approach includes an easier process for updating the maintenance application 805 since only one version is hosted on the server 212. Additionally, the user device 210 will not be required to have the maintenance application 805 installed, and hosting the maintenance application 805 provides broader compatibility among device platforms.

Figure 9:
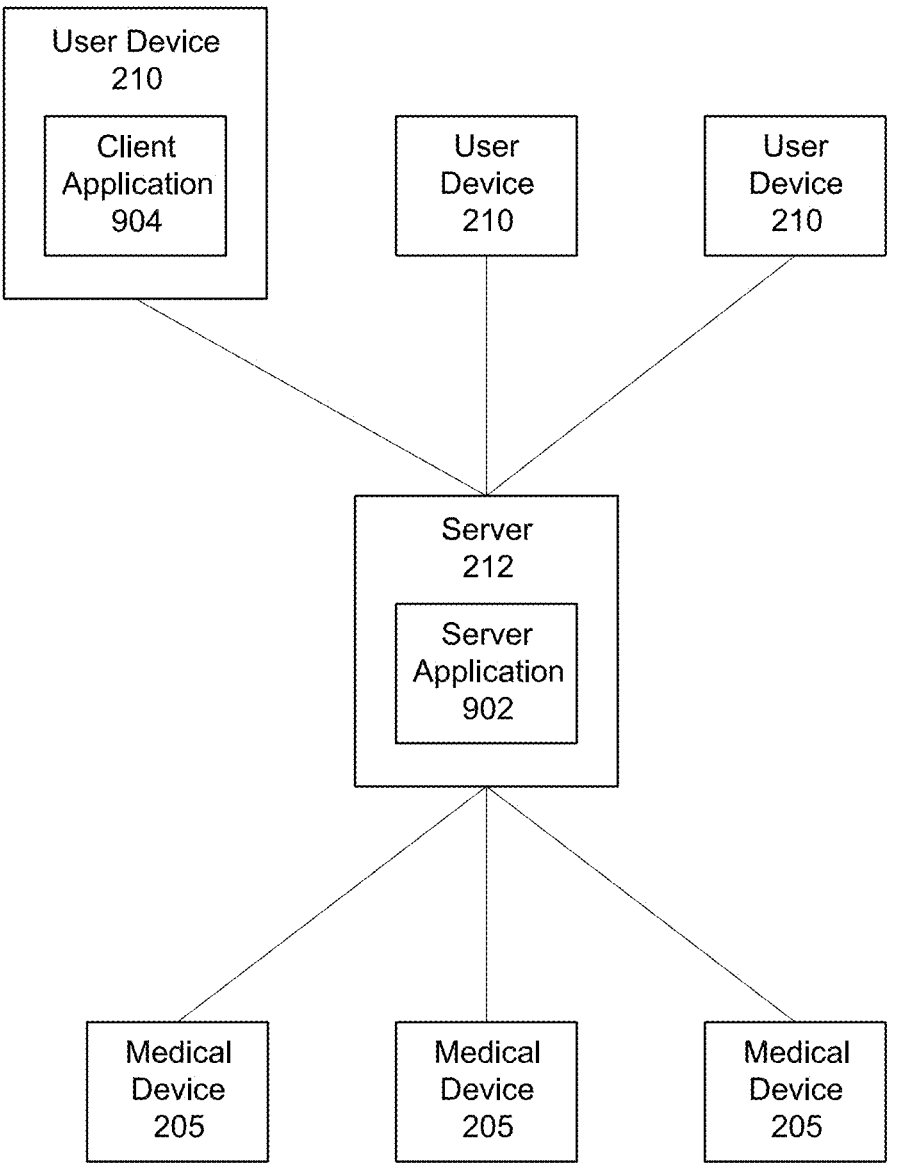
FIG. 9 shows an example block diagram of a maintenance system where the user device communicates with a medical device through a server.

As discussed above, the server 212 in communication with the medical device 205 may allow a user to perform operations relating to the medical device 205 remotely (for example, remotely view status information of the medical device 205, remotely operate the medical device 205, and/or the like). In some embodiments, a user at the user device 210 can access the medical device 205 through the server 212 instead of communicating with the medical device 205 directly using the user device 210. FIG. 9 illustrates an example block diagram of the maintenance system 200 where the user device 210 communicates with the medical device 205 through the server 212. In some embodiments, the server 212 communicates with the medical device 205 through a network, such as the Internet, WLAN, LAN, and/or the like.

In some embodiments, the user device 210 communicates with the medical device 205 by accessing a server application 902 on the server 212 through a client application 904. In some embodiments, the client application 904 may be implemented using the client component 810. In some embodiments, the client application 904 may be implemented using a web browser. In some embodiments, the server application 902 may generate one or more pages that may be displayed to the user by the client application 904 via the user interface 230 of the user device 210. In other embodiments, the client application 904 may generate one or more pages to be displayed to the user, using data received from the server application 902. A user at the user device 210 may need to perform one or more authentication procedures to access the server application 902 provided by the server 212, in order to monitor and/or perform operations on the medical device 205.

By having the user device 210 access the medical device 205 through the server 212, the user may be able monitor and/or perform operations on the medical device 205 remotely from any location, as long as a connection with the server 212 can be maintained. In addition, by accessing the server application 902 on the server 212, an amount of software implemented on the user device 210 may be reduced.

In some embodiments, a plurality of different user devices 210 may be used to access the medical device 205 through the server 212. In addition, the server 212 may be able to communicate with more than one medical device 205. As such, the server 212 may serve as a "central hub" connecting the various user devices 210 and the various medical devices 205. In some embodiments, this allows for updates to the server application 902 to be implemented at the server 212, without affecting the user devices 210 or the medical devices 205. In addition, updates to software or firmware on the user devices 210 or the medical devices 205 may be propagated through the server 212. In some embodiments, one or more authentication procedures may be used to allow the user device 210 to access the medical device 205. For example, the server 212 may be accessed by multiple user devices 210 and connected to multiple medical devices 205 associated with a plurality of different hospitals, and the user device 210 associated with a particular hospital may be able to access the medical devices 205 associated with the hospital through the server 212, but not medical devices associated with other hospitals.

In some embodiments, the server 212 may be owned or operated by an entity associated with the medical device 205, such as a manufacturer of the medical device 205, allowing for software or firmware for the medical devices 205 or the user devices 210 to be kept up to date by the manufacturer. For example, the manufacturer may be able to remotely update software or firmware of the medical devices 205 through the server 212. In addition, documentation or other information (for example, a product technical manual) associated with the medical device 205 may be maintained and kept up to date by the server 212, and provided to the user devices 210 and/or the medical devices 205 as needed. In some embodiments, the documentation or other information is aggregated at the server 212, whether owned by the manufacturer of the medical device 105, 205 or the hospital. The aggregated data could be used for asset tracking and other purposes. For example, a user wishing to perform a maintenance task on the medical device 205 (for example, an electrical safety check, a functional check, and/or the like) may access the server 212 in order to obtain the most up-to-date documentation on how to perform the task. In some embodiments, the maintenance software application 805 may be maintained and kept up to date by the server 212.

In some embodiments, the server 212 may receive and analyze status information from one or more medical devices 205. The status information can be used to assess maintenance needs of the medical devices 205. For example, in some embodiments, the server 212 may use received status information to determine an operational status or remaining operational life of a component of the medical device 205, which can be used to assess whether or not the component needs to be replaced. If a determination is made that the component should be replaced, the user may be prompted to order replacement components for the medical device 205.

Figure 10:
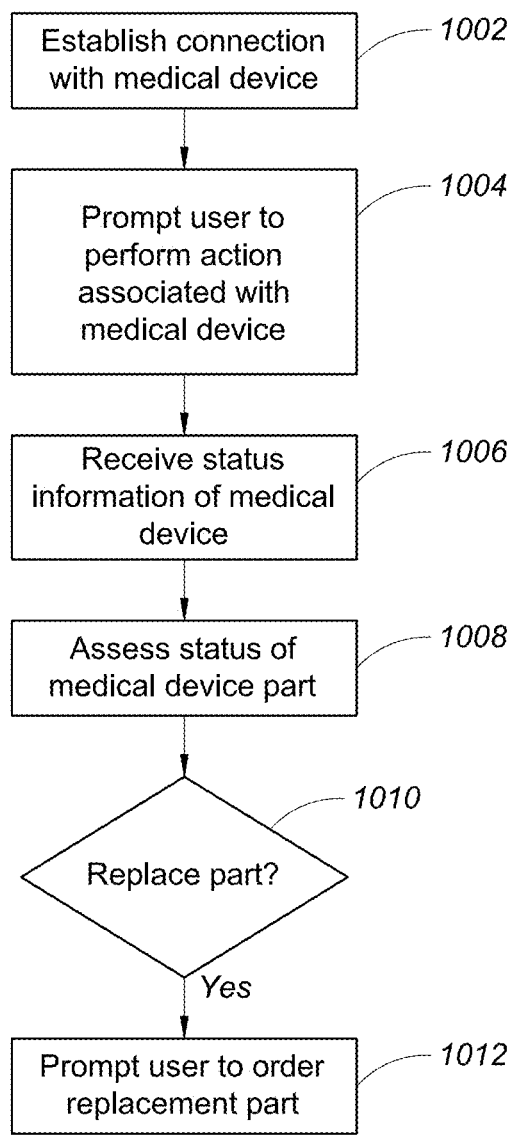
FIG. 10 shows a flowchart of an example process for ordering replacement components for a medical device, based upon received status information of the medical device.

FIG. 10 illustrates an example flowchart of a method 1000 for ordering replacement components for the medical device 205, based upon received status information of the medical device 205. At block 1002, the server 212 establishes a connection between the user device 210 and the medical device 205. In some embodiments, the connection is established in response to authentication information being received from the user device 210, whereupon the server 212 authenticates the user device 210 and verifies that the user device 210 is authorized to connect with the medical device 205.

At block 1004, a user may be optionally prompted to perform an action associated with the medical device 205. In some embodiments, prompting the user may comprise generating and displaying screen elements on the user interface 225, 230, 232 comprising instructions to perform the action. In some embodiments, the action may be performed by the user using the user interface 225 of the user device 210 and may comprise one or more interactive elements that enable or assist the user to perform the action. For example, the user may be prompted to input one or more parameters and/or press a button to initiate a diagnostic procedure to be performed by the medical device 205. In some embodiments, the user may be able to perform the action remotely from the medical device 205, using the user interface 230 of the user device 210.

In some embodiments, the action may comprise a physical action to be performed on the medical device 205 (for example, connecting a cable, flipping a switch, reading a display screen, or the like). For example, the user may be presented with a user interface prompt (for example, on the user interface 225, 230 of the medical device 205 or the user device 210) to perform the action on the medical device 205. In some embodiments, the action may comprise a combination of an action performed on the user interface 225, 230 and a physical action performed on the medical device 205.

In some embodiments, the server 212 may receive an indication that the user has performed the action. The verification may comprise the user providing input on the user interface 125, 130 indicating that they have performed the action, a detection by the server 212 of a status condition of the medical device 205 consistent with the action having been performed (for example, receiving a signal from the medical device 205 indicating that a diagnostic procedure has been initiated), or a combination thereof.

At block 1006, status information relating to the medical device 205 is received. In some embodiments, the status information is received in response to the user performing an action (for example, at block 1004). The status information may comprise information sent by the medical device 205 to the server 212, such as electrical measurements, diagnostic measurements, test results, and/or the like. In some embodiments, status information may be received from a user within proximity of the medical device 205, the status information being provided by the user on the user interface 225 (for example, based upon one or more observations or measurements made by the user with regards to the medical device 205).

At block 1008, based at least in part upon the received status information, a status of one or more components of the medical device 205 is determined. For example, the status information may comprise values of one or more measurements indicative of a status of a particular component, which may be aggregated in order to determine a status of the component. In some embodiments, the status of the component may indicate a particular state of the component (for example, whether the component is working or not). In some embodiments, the status information may be based upon the results of one or more tests. For example, a TCD test failure may indicate that a TCD circuit is in need of replacement (for example, by replacing a power PCB of the medical device). On the other hand, a failure of a thermal cutout test may indicate a need to replace a cutout (for example, by replacing the heater plate or the power PCB, depending upon the location of the cutout).

The status of the component may also comprise a remaining operational life of the component. For example, where the value of one or more measurements associated with a component change over time with component use in a predictable manner, the values may be compared to a look-up table or other data structure to determine a remaining operational life of the component. For example, the status of a component may indicate that its lifespan has expired or its remaining operational life does not exceed a threshold, and is thus in need of replacement. As an example for the respiratory humidifier 5, the status of the sensor cartridge 6 may indicate that the lifespan of the sensor cartridge 6 has expired or will soon expire.

In some embodiments, the status of the component may indicate that the component is obsolete. For example, versioning information may be maintained at the server and downloaded to the medical device or user device, from which a version mismatch may be detected. In some embodiments, a version mismatch for a software module may trigger a software download to update the software module. However, in some embodiments a version mismatch may require the replacement of one or more components. As an example for the respiratory humidifier 5, the sensor cartridge 6 may need to be replaced due to new functionality requiring a circuit change on a PCB of the sensor cartridge 6.

At block 1010, a determination is made as to whether at least one of the one or more assessed components of the medical device 205 should be replaced, based upon the assessed status of the components. For example, the determination may be made based upon a state of the component. In some embodiments, a component may be considered to be in need of replacement if the remaining operational life of the component is less than a threshold value (for example, less than 10% operational life remaining).

At block 1012, if it is determined that a component of the medical device 205 should be replaced, the user is prompted to order a replacement component. In some embodiments, this may comprise displaying one or more screen elements to the user on the user interface 230 of the user device 210, such as a button to order the component, a link to a store page associated with the component, and/or the like.

If the method 1000 for ordering replacement components for the medical device 205 is interrupted, a message, such as a modal message, may be displayed to the user indicating an interruption has occurred. In some embodiments, if the method 1000 for ordering replacement components for the medical device 205 is re-established, the method 1000 may continue from the point at which the interruption occurred.

In some embodiments, the method 1000 for ordering replacement components for the medical device 205 may start over.

The process for ordering replacement components for the medical device 205 is not limited to the order and number of steps described in FIG. 10. While the process for ordering replacement components for the medical device 205 according to FIG. 10 describes the execution of a series of steps in a particular sequence, the individual steps may be performed in any order, unless otherwise specified. Additionally, the process for ordering replacement components for the medical device 205 does not require execution of all the steps described in FIG. 10. In some embodiments, the process for ordering replacement components for the medical device 205 may include additional steps not described in FIG. 10. In some embodiments, the process for ordering replacement components for the medical device 205 may not include all steps described in FIG. 10.

In some embodiments, the server 212 may be configured to order components for the medical device 205 automatically in response to a determination that the component is in need to replacement, allowing for hospitals and medical personnel to better concentrate on patient care without having to worry about making sure that needed components will always be available.

Figure 11:
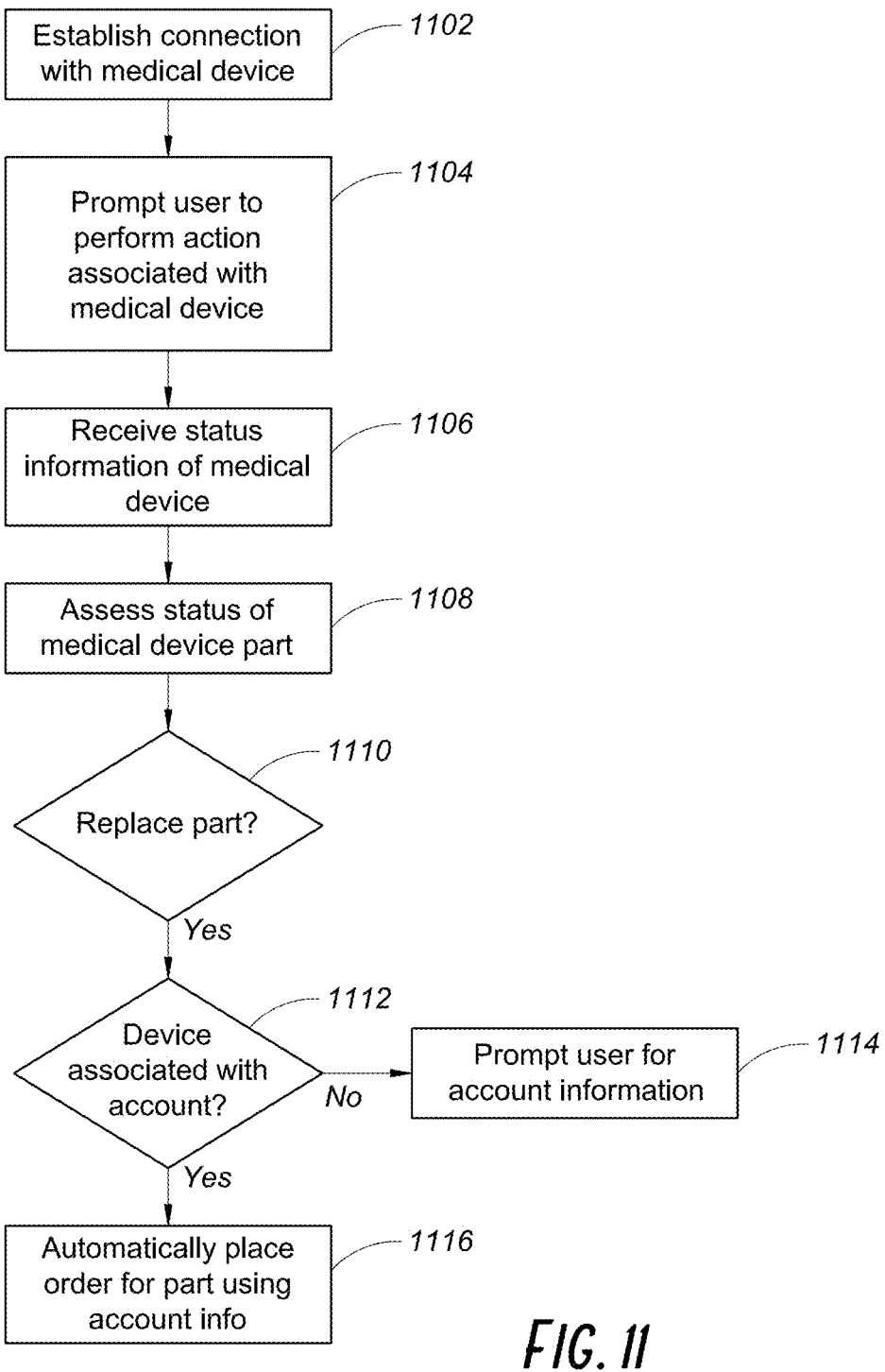
FIG. 11 shows another flowchart of an example process for ordering replacement components for a medical device, based upon a received status information of the medical device.

FIG. 11 illustrates a flowchart of an example process for automatically ordering components for the medical device 205. At block 1102, the server 212 establishes a connection between the user device 210 and the medical device 205. At block 1104, a user may optionally be prompted to perform an action associated with the medical device 205. The action may be performed on the user interface 225, 230 of the medical device 205 or the user device 210, physically performed on the medical device 205, or some combination thereof. At block 1106, status information of the medical device 205 may be received by the server 212, which may be used to assess a status of one or more components of the medical device 205 at block 1108. At block 1110, a determination is made as to whether a component of the one or more components should be replaced. In some embodiments, blocks 1102 through 1110 may be similar to blocks 1002 through 1010.

At block 1112, a determination may be made as to whether the medical device 205 is associated with an account. An account may correspond to a user, a hospital, or other entity able to purchase the medical device 205 and/or components of the medical device 205. Accounts may be associated with payment information, delivery information, and/or the like.

At block 1114, if the medical device 205 is not associated with an account, the user may be prompted for account information. The account information may comprise payment information, delivery information, and/or the like. An order for the component may then be placed using the received account information. In addition, the account information can be stored by the server 212 to be used for future component purchases.

On the other hand, if the medical device 205 is determined to be associated with an account, then at block 1116, an order for the component may be placed automatically, based upon stored account information associated with the account. In some embodiments, a user (for example, the user at the user device 210, or a different user associated with the account) may be prompted to confirm the ordering of the component. For example, a message may be sent to a purchasing department of the hospital associated with the account, which may then confirm the component order. In some embodiments the automatic replacement order may be sent to a server, such as server 212, which may be owned by the manufacturer of the medical device. In this way the manufacturer automatically receives replace orders and can ship out replacement components or medical devices when required.

If the process for automatically ordering components for the medical device 205 is interrupted, a message, such as a modal message, may be displayed to the user indicating an interruption has occurred. In some embodiments, if the process for automatically ordering components for the medical device 205 is re-established, the process may continue from the point at which the interruption occurred. In some embodiments, the process for automatically ordering components for the medical device 205 may start over.

The process for automatically ordering components for the medical device 205 is not limited to the order and number of steps described in FIG. 11. While the process for automatically ordering components for the medical device 205 according to FIG. 11 describes the execution of a series of steps in a particular sequence, the individual steps may be performed in any order, unless otherwise specified. Additionally, the process for automatically ordering components for the medical device 205 does not require execution of all the steps described in FIG. 11. In some embodiments, the process for automatically ordering components for the medical device 205 may include additional steps not described in FIG. 11. In some embodiments, the process for automatically ordering components for the medical device 205 may not include all steps described in FIG. 11. One or more steps of the process for automatically ordering components for the medical device 205 may be executed by any one of or any combination of the processors 115, 215, 120, 220, 222 or other processors residing in the same devices or other devices.

In some embodiments, how components are ordered may be configurable for different components. For example, in some embodiments, components under a certain price threshold may be ordered automatically, while components above the price threshold may require confirmation by one or more authorized users.

In some embodiments, the server 212 may receive information from multiple medical devices 205. In addition to performing tasks and ordering components for the medical device 205, in some embodiments the information received from multiple medical devices 205 can be aggregated in order to determine usage trends for the multiple medical devices 205. These usage trends may be used to identify common errors associated with the medical device 205, adjust production of the medical device 205 or related products and components, and/or the like.

Figure 12:
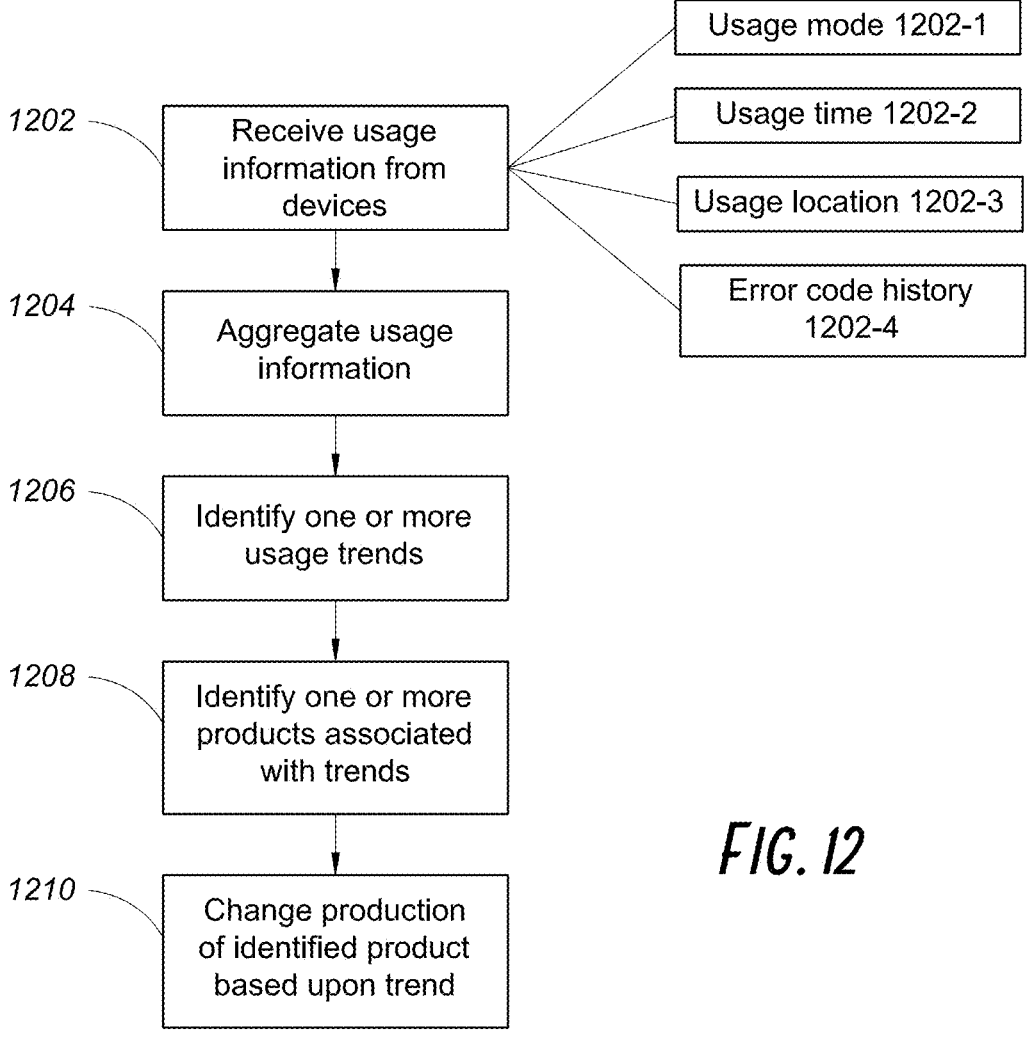
FIG. 12 shows a flowchart of an example process for adjusting production based upon analyzed usage trends of medical devices.

FIG. 12 illustrates a flowchart of an example process for adjusting production based upon analyzed usage trends of one or more medical devices 205. At block 1202, usage information is received from one or more medical devices 205. In some embodiments, the usage information is collected by the server 212. In some embodiments, usage information may be collected by multiple servers 212. The usage information may comprise usage mode information 1202-1, usage time information 1202-2, usage location information 1202-3, error code history 1202-4, and/or the like. In some embodiments, usage information may also comprise status information as described above.

Usage mode information 1202-1 may refer to one or more operating settings of the medical device 205. In some embodiments, the medical device 205 may be run in one of a plurality of different operating modes. For example, when the medical device 205 is a humidifier, it may be used in a plurality of different discrete modes, such as an invasive mode, a non-invasive mode, a neonatal mode, and/or the like. In some embodiments, usage mode information 1202-1 may refer to different combinations of settings with which the medical device 205 may be run. For example, a humidifier device, in addition to one or more discrete modes, may have a humidity setting that can be set to a plurality of different values.

Usage time information 1202-2 may refer to a time period that the medical device 205 is in use (for example, how long the medical device 205 is in use, how often the medical device 205 is in use, and/or the like). In some embodiments, usage time information 1202-2 may include what times the medical device 205 is in usage (for example, morning, afternoon, or night).

Usage location information 1202-3 may refer to a location of the medical device 205 where it is operating. In some embodiments, the usage location information 1202-3 may comprise geographic location. In some embodiments, the usage location information 1202-3 may comprise a location type where the medical device 205 is operated (for example, which ward in a hospital).

Error code history 1202-4 may refer to errors experienced by the medical device 205 during the course of operation, and may comprise error information automatically detected by the medical device 205, the server 212, and/or the user device 210, or error information entered by a user on the user interface 225, 230, 232, based upon one or more user observations.

In some embodiments, one or more types of usage information may be combined or correlated, to form a more complete picture of the usage of the medical device 205. For example, usage mode information 1202-1 and usage time information 1202-2 may be correlated in order to analyze what modes the medical device 205 is typically run in during different time periods (for example, the medical device 205 may be run more often in a first mode in the morning, and in a second mode at night).

In some embodiments, the usage information may be collected while one or more of the medical devices 205 are running standalone (for example, not connected to a server or user device). When the medical device 205 is connected to a server or user device, the collected usage information can be batched and uploaded to the server or user device. In some embodiments, usage information received by a user device may be batched and uploaded to a server (for example, if the user device is not connected to the server when interfacing with the medical device, but connects to the server at a later time).

At block 1204, collected usage information from multiple medical devices 205 can be combined or aggregated. In some embodiments, multiple medical devices 205 may be connected to the server 212, which receives and aggregates usage information from each of the connected medical devices 205. In some embodiments, usage information collected by multiple servers 212 may be transmitted to and aggregated at one or more "hub" servers. For example, the server 212 may be associated with the medical devices 205 operating within a particular geographic region, or associated with a particular medical provider. Usage information collected by the server 212 may be transmitted to a hub server to be aggregated with usage information collected by other servers corresponding to other geographic regions or medical providers.

At block 1206, the aggregated usage information is used to identify one or more usage trends. In some embodiments, a usage trend may indicate changes in usage of the medical device 205 over time (for example, decrease in usage of the medical device 205 at night over last three months, increase in usage of the medical device 205 in neonatal mode over past year, and/or the like). The one or more usage trends may be based upon any category of the collected usage information, or a combination thereof.

At block 1208, one or more products associated with the usage trends are identified. In some embodiments, the one or more products may comprise components of the medical device 205 that are associated with certain types of usage (for example, usage modes, usage location, and/or the like). In some embodiments, the one or more products may comprise other devices related to usage of the medical device 205. For example, products related to premature birth and infant care may be identified as being related to the neonatal mode usage of the medical device 205.

At block 1210, a production characteristic of an identified product is changed, based at least in part upon the one or more identified usage trends. In some embodiments, a production quantity of the identified product may be increased or decreased, in response to the identified usage trend. For example, if it is found that the medical device 205 is frequently used in neonatal mode, the production quantity of products related to premature birth and infant care (for example, an infant circuit kit) may be increased. In some embodiments, a production quantity of a product may be changed based upon geographic (for example, increased or decreased production in certain geographic regions, based upon usage trends within those regions). In some embodiments, a change in a production characteristic of a product may comprise changing a feature of the product in response to the identified usage trends. For example, if the medical device 205 is found to only be operated in a particular usage mode, a new product specializing in that usage mode may be produced. In an alternative form, the production characteristic may relate to ordering of medical devices or components of the medical device. For example a hospital may be instructed to modify purchasing patterns based on the identified usage trends.

If the process for adjusting production based upon analyzed usage trends of one or more medical devices 205 is interrupted, a message, such as a modal message, may be displayed to the user indicating an interruption has occurred. In some embodiments, if the process for adjusting production based upon analyzed usage trends of one or more medical devices 205 is re-established, the process may continue from the point at which the interruption occurred. In some embodiments, the process for adjusting production based upon analyzed usage trends of one or more medical devices 205 may start over.

The process for adjusting production based upon analyzed usage trends of one or more medical devices 205 is not limited to the order and number of steps described in FIG. 12. While the process for adjusting production based upon analyzed usage trends of one or more medical devices 205 according to FIG. 12 describes the execution of a series of steps in a particular sequence, the individual steps may be performed in any order, unless otherwise specified. Additionally, the process for adjusting production based upon analyzed usage trends of one or more medical devices 205 does not require execution of all the steps described in FIG. 12. In some embodiments, the process for adjusting production based upon analyzed usage trends of one or more medical devices 205 may include additional steps not described in FIG. 12. In some embodiments, the process for adjusting production based upon analyzed usage trends of one or more medical devices 205 may not include all steps described in FIG. 12. One or more steps of the process for adjusting production based upon analyzed usage trends of one or more medical devices 205 may be executed by any one of or any combination of the processors 115, 215, 120, 220, 222 or other processors residing in the same devices or other devices. Any one or more of the maintenance methods disclosed above can be executed by the medical device, in particular the humidifier 5. The humidifier 5 is further advantageous because it can also run self diagnostics using one or more of the maintenance methods described above. The humidifier 5 may be configured to run any one or more of the maintenance methods described earlier at regular time intervals to ensure correct operation of the humidifier 5, or alert the user if there is a fault or other anomaly.

Unless the context clearly requires otherwise, throughout the description and the claims, the words "comprise", "comprising", and the like, are to be construed in an inclusive sense as opposed to an exclusive or exhaustive sense, that is to say, in the sense of "including, but not limited to".

Reference to any prior art in this specification is not, and should not be taken as, an acknowledgement or any form of suggestion that that prior art forms part of the common general knowledge in the field of endeavor in any country in the world.

The disclosed apparatus and systems may also be said broadly to consist in the parts, elements and features referred to or indicated in the specification of the application, individually or collectively, in any or all combinations of two or more of said parts, elements or features.

Where, in the foregoing description reference has been made to integers or components having known equivalents thereof, those integers are herein incorporated as if individually set forth.

It should be noted that various changes and modifications to the presently preferred embodiments described herein will be apparent to those skilled in the art. Such changes and modifications may be made without departing from the spirit and scope of the disclosed apparatus and systems and without diminishing its attendant advantages. For instance, various components may be repositioned as desired. It is therefore intended that such changes and modifications be included within the scope of the disclosed apparatus and systems. Moreover, not all of the features, aspects and advantages are necessarily required to practice the disclosed apparatus and systems. Accordingly, the scope of the disclosed apparatus and systems is intended to be defined only by the claims that follow.

What is claimed is:

1. A method of automatically initiating the execution of one or more maintenance tasks for a flow generator and a humidifier of a medical device, the medical device comprising a system health protection component configured to respond to an unexpected condition, wherein the system health protection component comprises a transient current detector and a thermal cutout and the one or more maintenance tasks comprise a functional check including validating an operation of the system health protection component of the medical device, the method comprising executing the one or more maintenance tasks by:

generating or simulating, by a processor, an unexpected condition, the unexpected condition comprising a transient current, an overcurrent, or supplying power to a heating element of the medical device;

providing, by the processor, a signal associated with the unexpected condition to the system health protection component;

determining, by the processor, a response of the system health protection component to the unexpected condition by measuring an electrical value in the system health protection component and the heating element of the medical device, the medical device comprising the flow generator and the humidifier; and based at least in part on the response, providing, by the processor, a result that the system health protection component does not successfully recognize the unexpected condition, incorrectly identifies the unexpected condition, or is too slow to recognize the unexpected condition, wherein the method further comprises using hardware and software of the medical device to generate or simulate the unexpected condition to test both hardware and software responses of the system health protection component.

2. The method of claim 1, wherein determining the response of the system health protection component is based on the processor determining whether the transient current detector has activated a current interrupter and/or the thermal cutout has tripped or a timer has exceeded a predetermined maximum time value.

3. The method of claim 2, wherein the processor determining the timer has exceeded a predetermined maximum time value comprises: comparing, by the processor an elapsed time between the generation of the unexpected condition and a triggering of the system health protection component to a predetermined threshold.

4. The method of claim 1, wherein some or all of the steps are performed at a server in communication with the medical device, at a user device in communication with the server and/or the medical device, and/or at the medical device.

5. The method of claim 1, further comprising determining if the one or more maintenance tasks have recently been performed.

6. The method of claim 1, further comprising: prompting a user to set up the one or more maintenance tasks via a user interface;

determining whether the user properly set up the one or more maintenance tasks;

executing the one or more maintenance tasks; and displaying one or more results of the one or more maintenance tasks to the user via the user interface.

7. The method of claim 1, wherein the one or more maintenance tasks further comprise one or more of: an electrical safety check, a system health protection check, and a second functional check.

8. The method of claim 7, wherein said electrical safety check comprises evaluating an electrical functionality of the medical device, the method further comprising:

determining, by the processor, whether the electrical safety check passed;

presenting a user with one or more troubleshooting suggestions via a user interface of the medical device or a user interface of a user device in response to an electrical safety check failure; and prompting the user to indicate whether the one or more troubleshooting suggestions identified the reason for the electrical safety check failure.

9. The method of claim 7, wherein said functional check comprises validating an operation of one or more mechanical components of the medical device, the one or more mechanical components comprising: a touch screen, a button, a color display, a speaker, and a light-emitting diode.

10. The method of any of claim 9, further comprising:

executing a speaker test;

executing a therapy touch screen test;

determining whether the therapy touch screen test passed;

executing a mute touch screen test in response to passing the therapy touch screen test;

executing a color display test; and executing a light-emitting diode test.

11. The method of claim 1, wherein the system health protection component comprises the thermal cutout, the method further comprising:

resetting the thermal cutout in response to the thermal cutout being tripped;

resupplying power to the heating element;

determining whether the thermal cutout reset; and displaying one or more results of the one or more maintenance tasks to a user via a user interface of the medical device or a user interface of a user device.

12. The method of claim 1, wherein the system health protection component comprises the thermal cutout, the method further comprising:

determining whether the thermal cutout failed to trip; and displaying one or more results of the one or more maintenance tasks to a user via a user interface of the medical device or a user interface of a user device, in response to the thermal cutout failing to trip.

13. The method of claim 1, comprising:

generating user interface information to cause one or more first user interface elements to be displayed by a user interface of a user device, the one or more first user interface elements prompting a user of the user device to perform an action;

receiving status information from a processor of the medical device in response to the action;

using the received status information to determine a status of a component of the medical device; and determining whether the component is in need of replacement based upon the determined status.

14. The method of claim 13, wherein the status of the component comprises a remaining operational life of the component and wherein determining whether the component is in need of replacement comprises determining if the remaining operational life of the component is under a threshold value.

15. The method of claim 13, further comprising determining whether the medical device is associated with an account information.

16. The method of claim 13, further comprising prompting the user to order a replacement component for the medical device in response to a determination that the component is in need of replacement, or automatically initiating an order for the replacement component for the medical device in response to the determination that the component is in need of replacement.

17. The method of claim 16, wherein automatically initiating an order for the replacement component for the medical device comprises generating user interface information to cause one or more second user interface elements to be displayed by a user interface of a second user device associated with a second user, the one or more second user interface elements prompting the second user to confirm the order.

18. The method of claim 13, wherein the action comprises the user inputting one or more parameters at the user interface of the user device, the one or more parameters used to perform one or more diagnostic procedures on the medical device.

19. The method of claim 1, further comprising executing multiple maintenance tasks in sequence, multiple maintenance tasks in synchrony, or any combination thereof.

20. The method of claim 1, wherein the signal comprises a signal that the system health protection component would be expected to detect as unexpected.

5

* * * * *